(12) United States Patent
Zaccaria

(10) Patent No.: US 10,098,776 B2
(45) Date of Patent: Oct. 16, 2018

(54) MULTI-DIRECTIONAL SUPPORT SYSTEM WITH FLEX SUPPORT BARS FOR USE ON FOOTWEAR

(71) Applicant: Gary Zaccaria, West Jordan, UT (US)

(72) Inventor: Gary Zaccaria, West Jordan, UT (US)

( * ) Notice: Subject to any disclaimer, the term of this patent is extended or adjusted under 35 U.S.C. 154(b) by 712 days.

(21) Appl. No.: 14/523,948

(22) Filed: Oct. 27, 2014

(65) Prior Publication Data

US 2016/0113802 A1 Apr. 28, 2016
US 2017/0325987 A9 Nov. 16, 2017

Related U.S. Application Data

(60) Provisional application No. 61/897,054, filed on Oct. 29, 2013.

(51) Int. Cl.
*A61F 5/01* (2006.01)
*A43B 7/20* (2006.01)
*A43B 7/32* (2006.01)

(52) U.S. Cl.
CPC .............. *A61F 5/0127* (2013.01); *A43B 7/20* (2013.01); *A43B 7/32* (2013.01); *A61F 5/012* (2013.01); *A61F 2240/001* (2013.01)

(58) Field of Classification Search
CPC .. A61F 5/00; A61F 5/01; A61F 5/0102; A61F 5/012; A61F 5/0127; A43B 7/18; A43B 7/20; A43B 7/32; A43B 5/00
USPC ................................ 602/27; 36/89, 102, 114
See application file for complete search history.

(56) References Cited

U.S. PATENT DOCUMENTS

| | | |
|---|---|---|
| 1,155,506 A | 10/1915 | Osaki |
| 1,205,206 A | 11/1916 | Hofmeister |
| 1,548,382 A | 8/1925 | Paul |
| 2,972,822 A | 2/1961 | Tanner |
| 3,613,273 A | 10/1971 | Marquis |
| 3,834,377 A | 9/1974 | Lebold |
| 4,719,926 A | 1/1988 | Nelson |
| 4,726,126 A | 2/1988 | Bernard |
| 4,753,229 A | 6/1988 | Sutherland |
| 4,766,681 A | 8/1988 | O'Rourke et al. |
| 4,776,111 A | 10/1988 | Crowley |
| 4,865,023 A | 9/1989 | Craythorne |
| 4,922,630 A | 5/1990 | Robinson |
| 4,977,891 A | 5/1990 | Grim |
| 4,982,733 A | 1/1991 | Broadhurst et al. |
| 4,989,350 A | 2/1991 | Bunch et al. |

(Continued)

*Primary Examiner* — Keri J Nelson

(57) ABSTRACT

A foot and ankle support system using one or more pressure-flexed support bars made of resilient material, each of which can be adjustably positioned and removably attached to selected positions along the medial, lateral, or posterior heel sides of an article of footwear. One end of the support bar is affixed to the base portion of the article of footwear and the other end is affixed to the collar or ankle portion causing the resilient support bar to flex into a bow-like position. Each support bar stores energy and returns resistance when engaged by various directional movements of the foot during walking, running, sports activities or rehabilitation. A plurality of pressure-flexed support bars work in tandem to provide additional support and control of foot inversion and eversion, pronation and supination. An alternative embodiment uses a pressure-flexed bladder type support bar filled with air, gas, liquid gel or other material.

25 Claims, 13 Drawing Sheets

(56) References Cited

U.S. PATENT DOCUMENTS

| | | | |
|---|---|---|---|
| 5,056,509 A | 10/1991 | Swearington | |
| 5,069,202 A | 12/1991 | Prock | |
| 5,109,613 A | 5/1992 | Van Dyke | |
| 5,125,171 A | 6/1992 | Stewart | |
| 5,152,082 A | 10/1992 | Culpepper | |
| 5,175,947 A | 1/1993 | Parracho | |
| 5,243,772 A | 9/1993 | Francis | |
| 5,317,820 A | 6/1994 | Bell | |
| 5,348,530 A | 9/1994 | Grim et al. | |
| 5,364,339 A | 11/1994 | Carver | |
| 5,400,529 A | 3/1995 | Bell | |
| 5,430,960 A | 7/1995 | Richardson | |
| 5,606,808 A | 3/1997 | Gilliard | |
| 5,672,056 A | 9/1997 | Fisher et al. | |
| 5,676,642 A | 10/1997 | Peters | |
| 5,765,298 A | 6/1998 | Potter | |
| 5,771,608 A | 6/1998 | Peterson | |
| 5,792,087 A * | 8/1998 | Pringle | A61F 5/0127 602/23 |
| 5,819,439 A | 10/1998 | Sanchez | |
| 5,836,903 A | 11/1998 | Peters | |
| 5,896,683 A | 4/1999 | Foxen | |
| 6,228,043 B1 | 5/2001 | Townsend et al. | |
| 6,279,252 B1 | 8/2001 | Pozzobon et al. | |
| 6,557,271 B1 | 5/2003 | Weaver, III | |
| 6,715,218 B2 | 4/2004 | Johnson | |
| 6,935,054 B2 | 8/2005 | Hall | |
| 7,020,989 B2 | 4/2006 | Kim | |
| 7,171,766 B2 | 6/2007 | Bouche et al. | |
| 7,243,444 B2 | 7/2007 | Seiner | |
| 7,334,354 B2 | 2/2008 | Foxen et al. | |
| 7,370,442 B2 | 5/2008 | Jung et al. | |
| 7,509,756 B2 | 3/2009 | Lebo | |
| 7,849,611 B2 | 12/2010 | Dean | |
| 8,245,419 B2 | 8/2012 | Echols | |
| 8,307,572 B2 | 11/2012 | Foxen | |
| 2005/0198869 A1 | 9/2005 | Bouche | |
| 2008/0082034 A1 | 4/2008 | Wilkerson | |
| 2009/0216167 A1 | 8/2009 | Harris | |
| 2013/0138031 A1* | 5/2013 | Bergmann | A43B 3/163 602/28 |
| 2014/0259799 A1* | 9/2014 | McDonnell, Jr. | A43B 7/20 36/140 |
| 2017/0087000 A1* | 3/2017 | Cain | A61F 5/0123 |

* cited by examiner

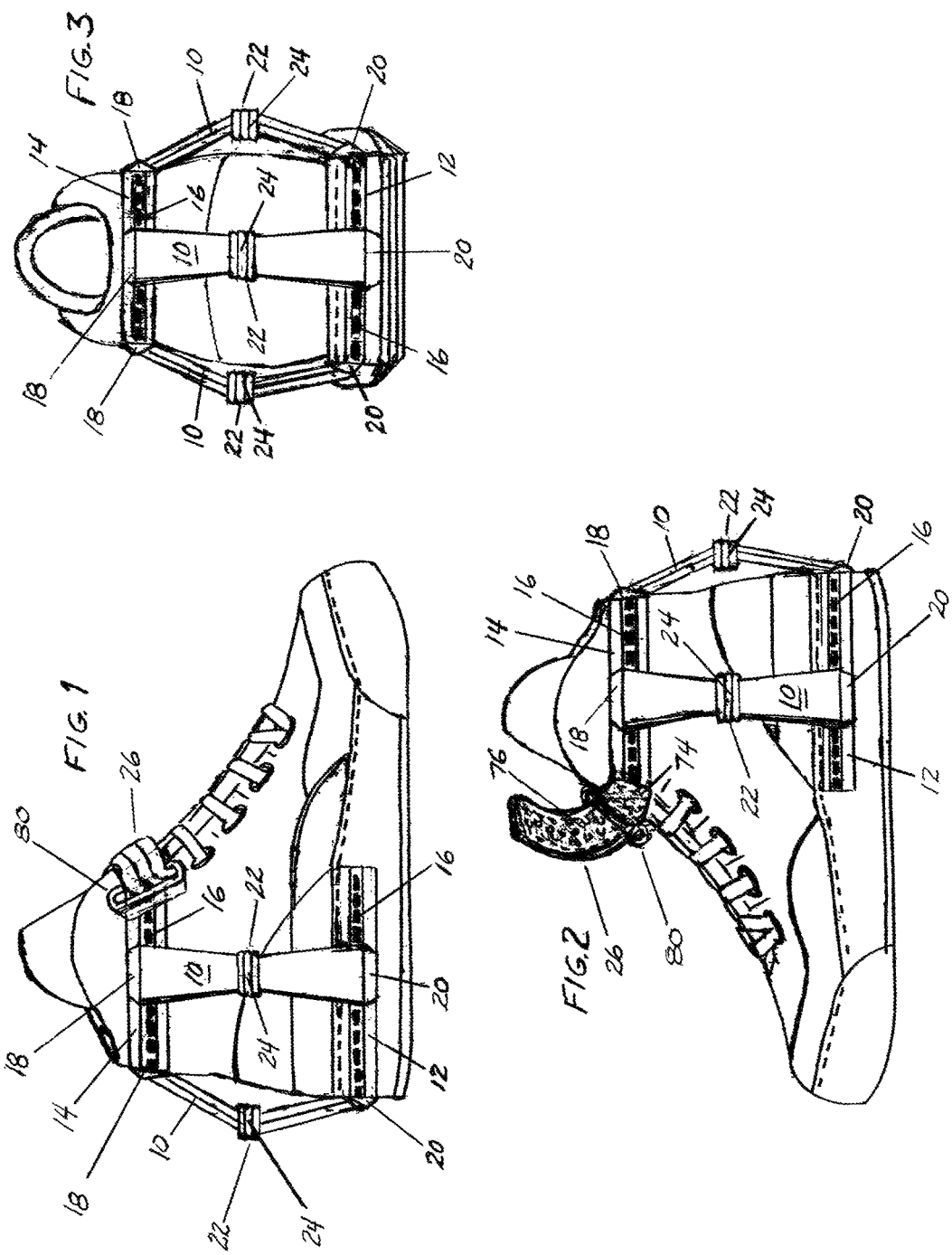

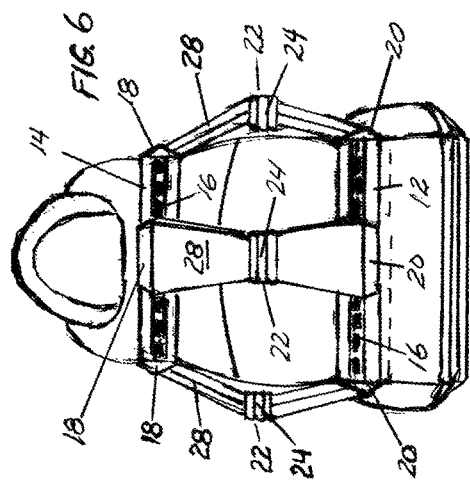
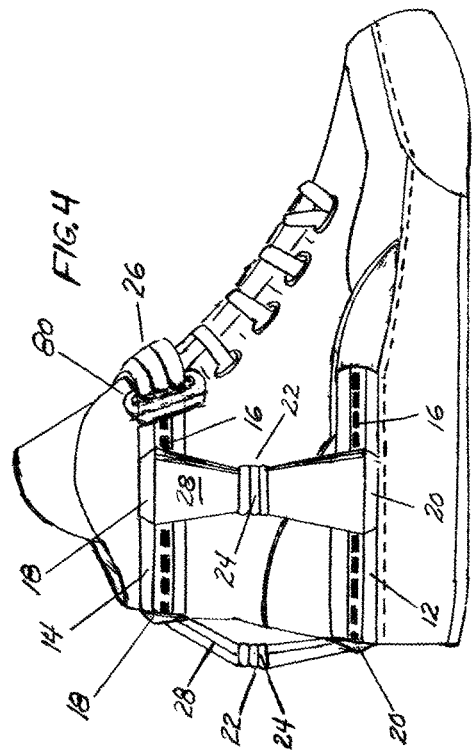
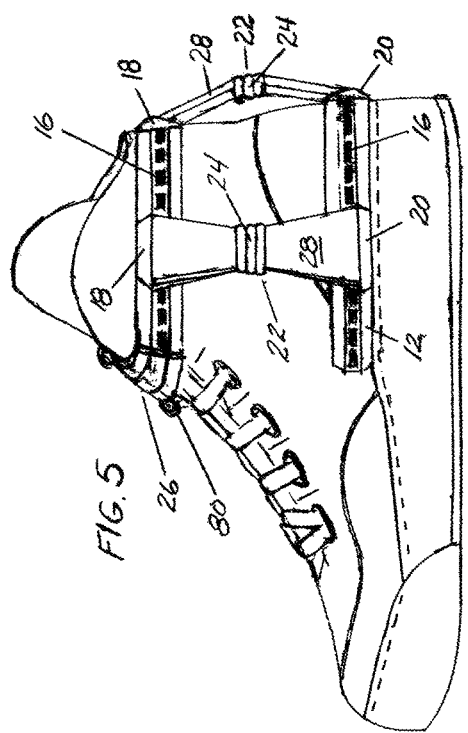

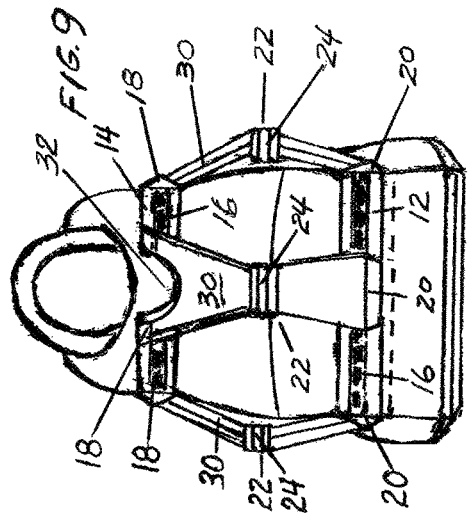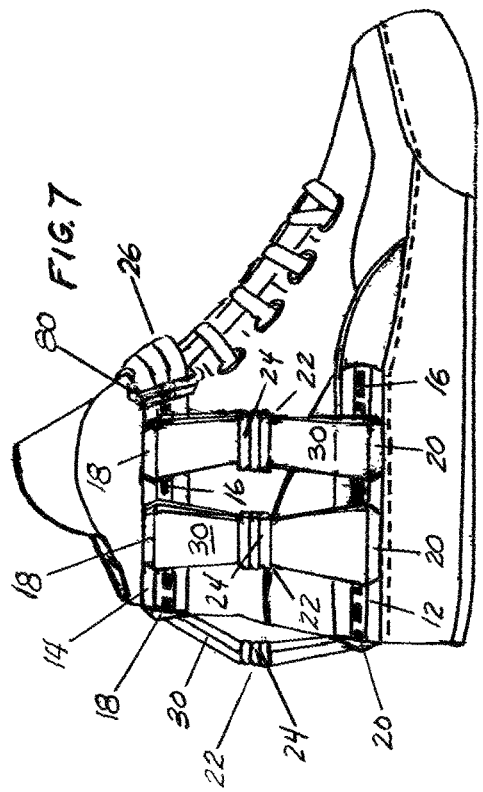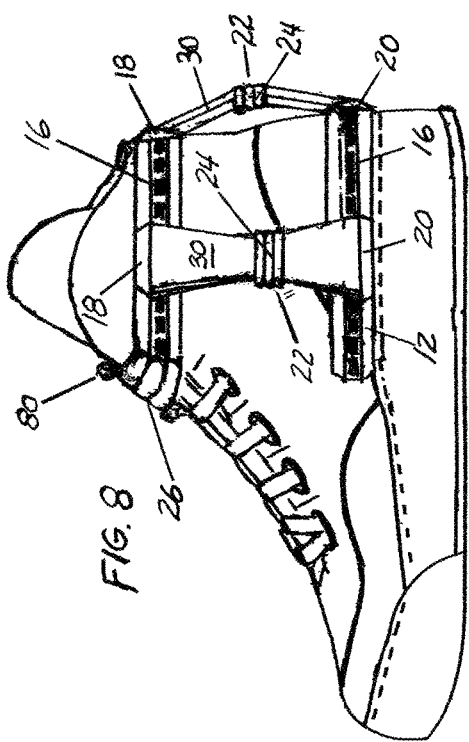

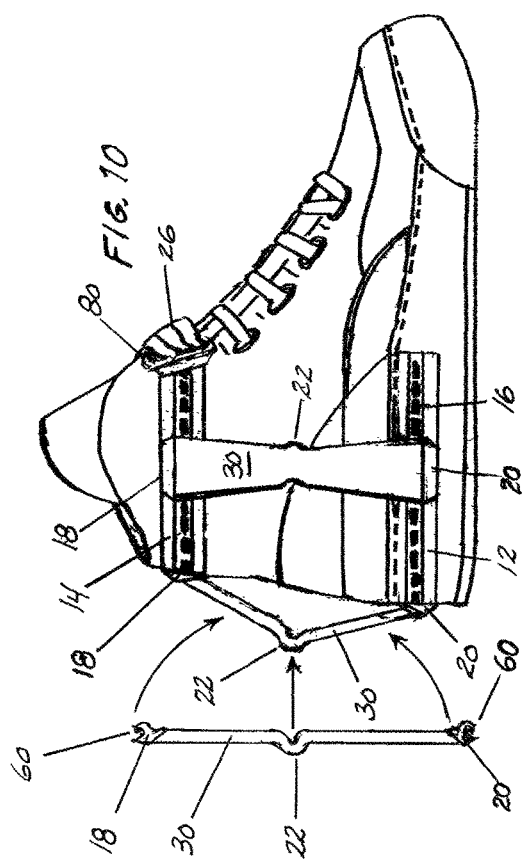
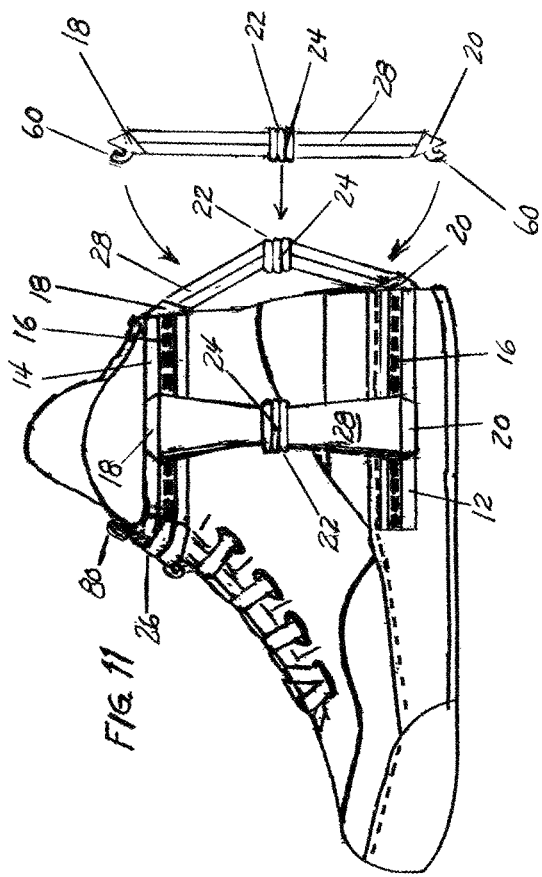

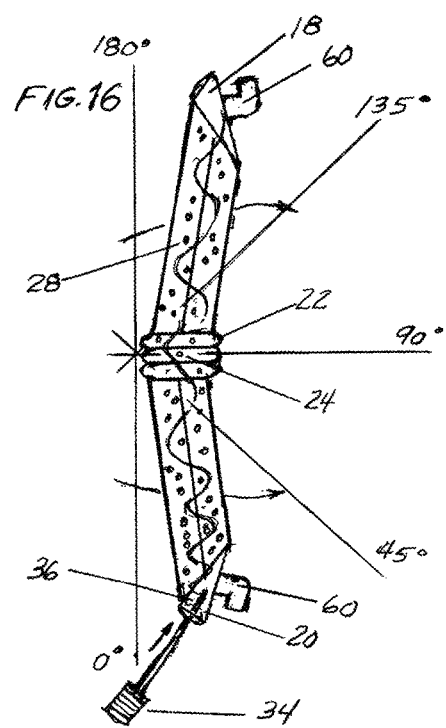
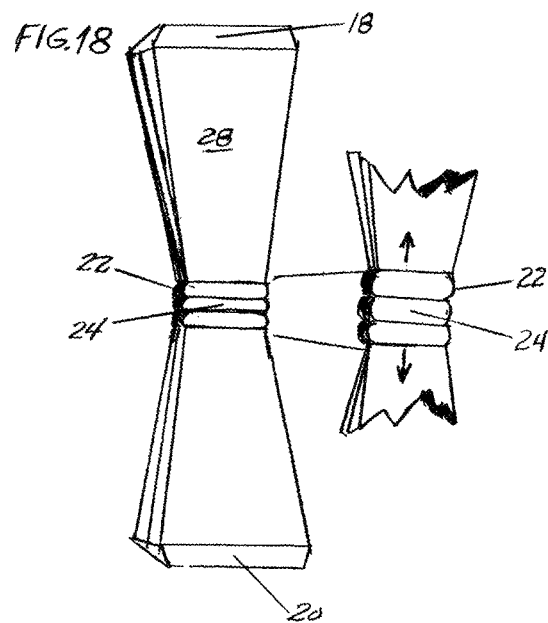
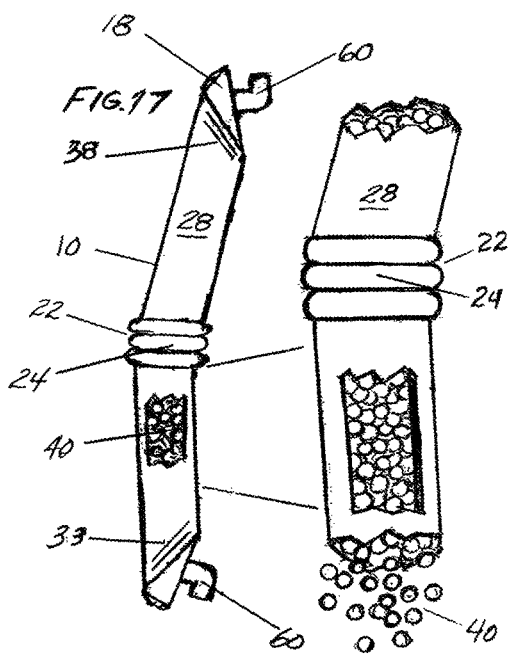
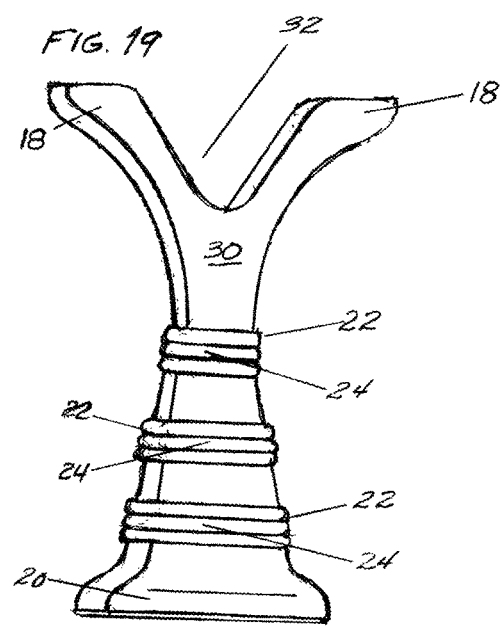

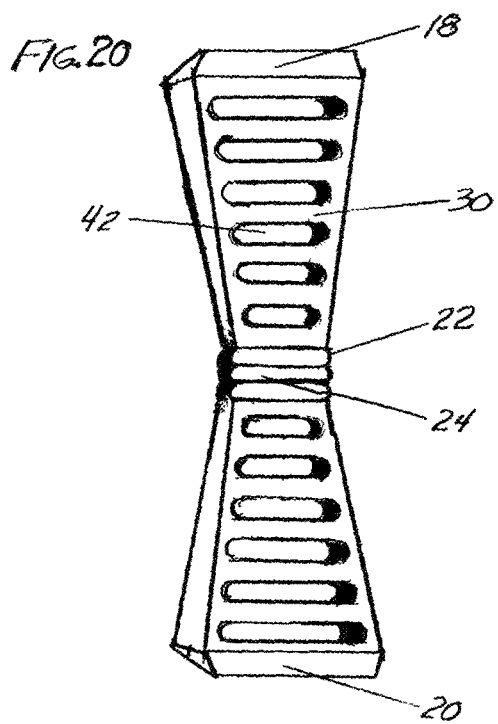
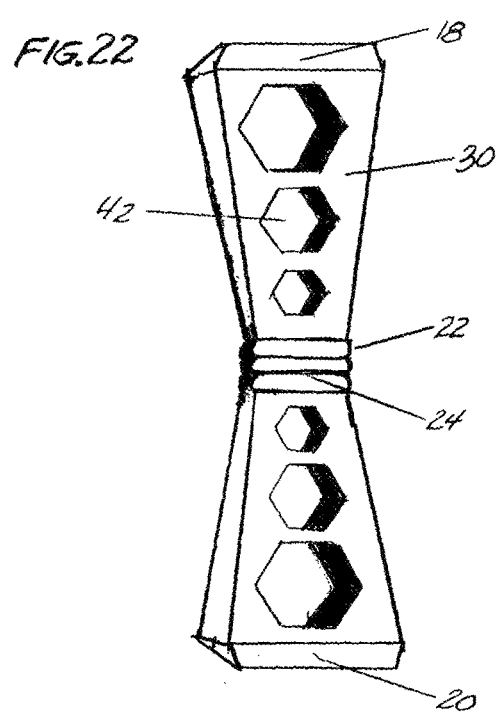
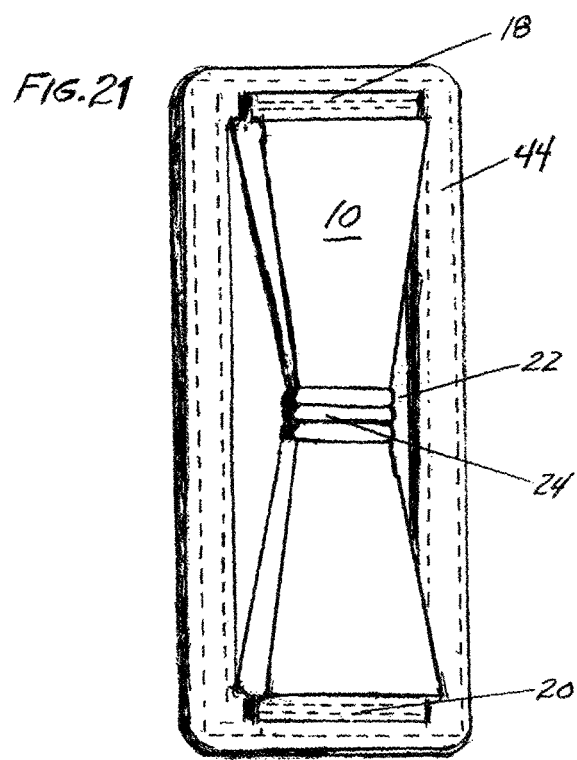
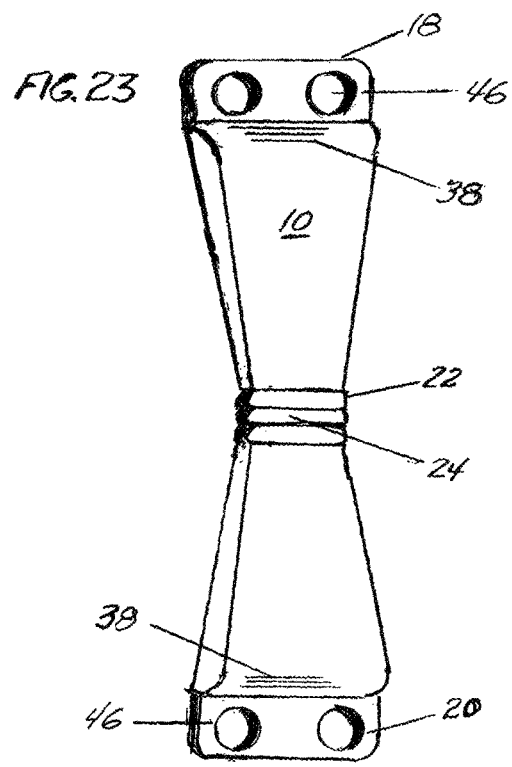

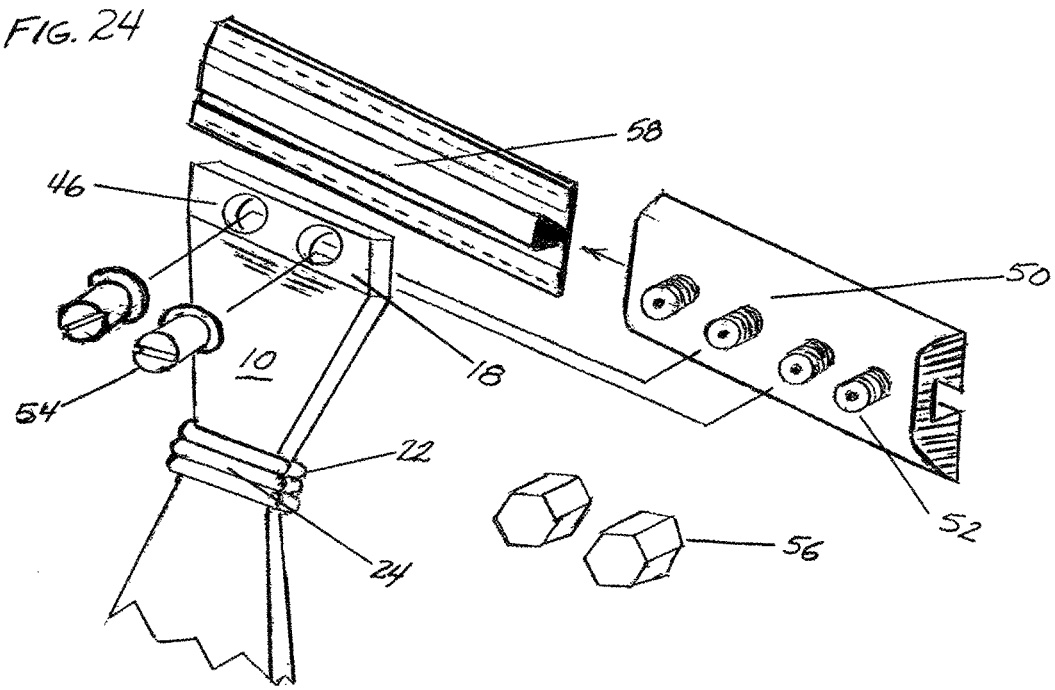
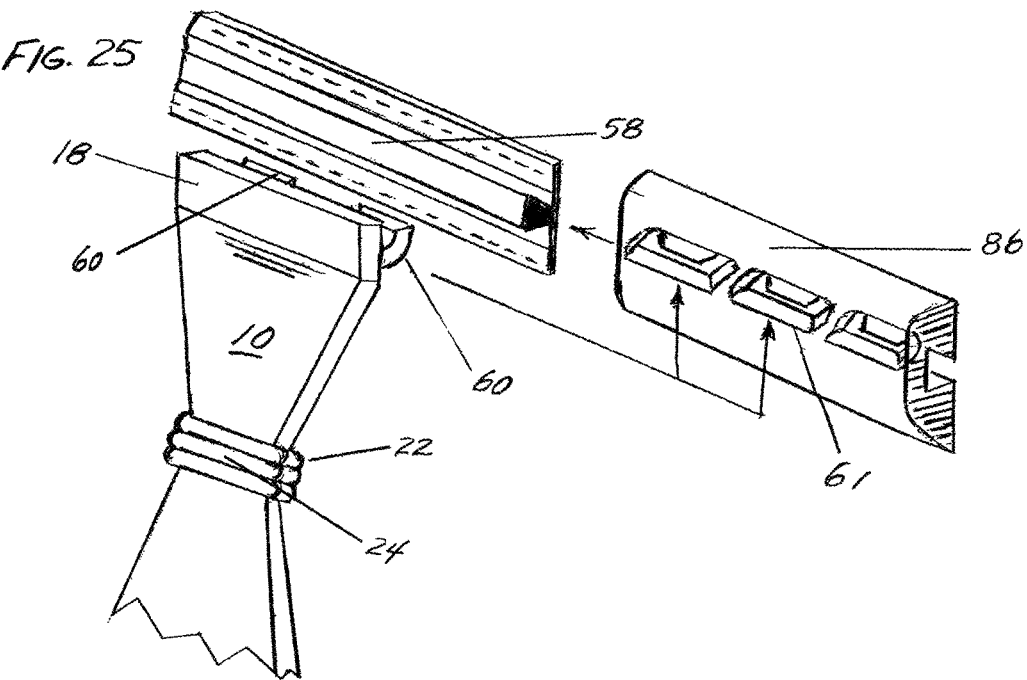

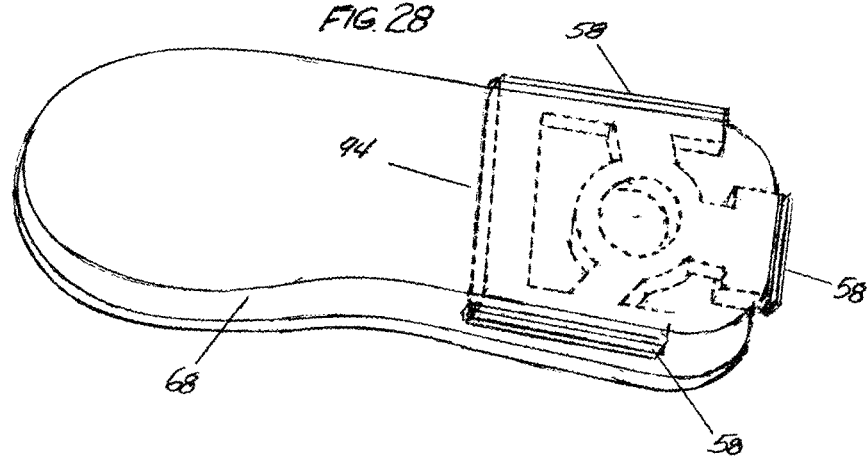
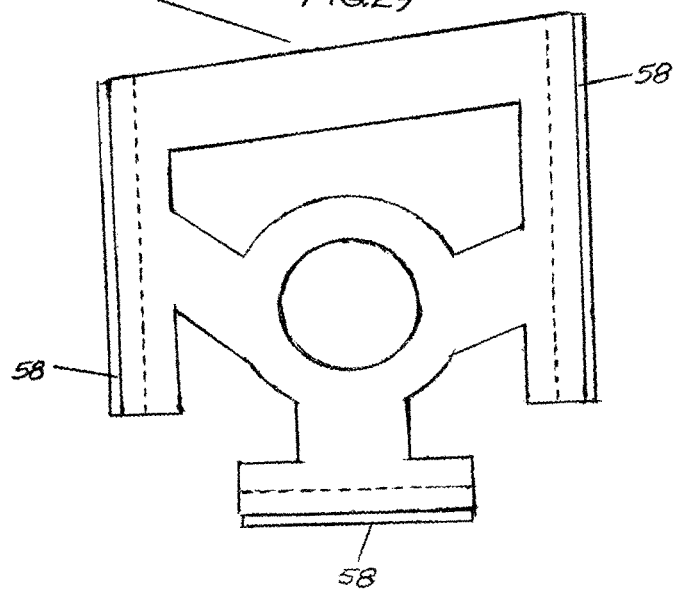
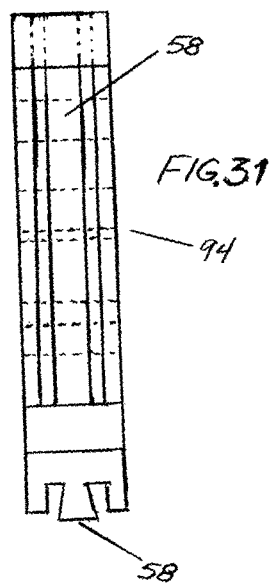
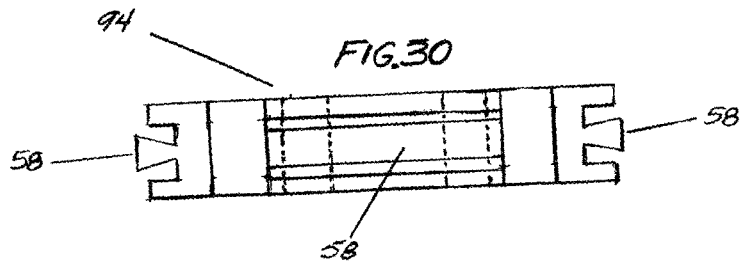

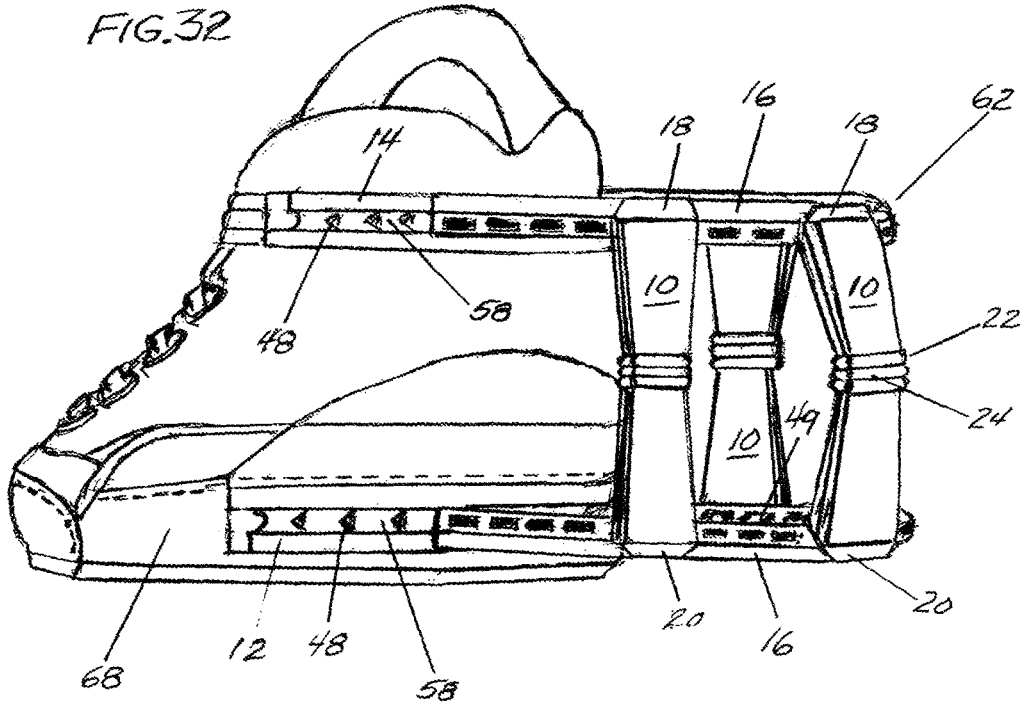

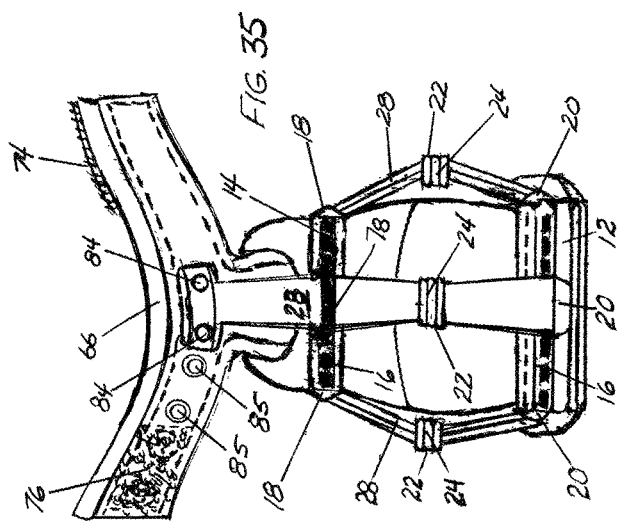
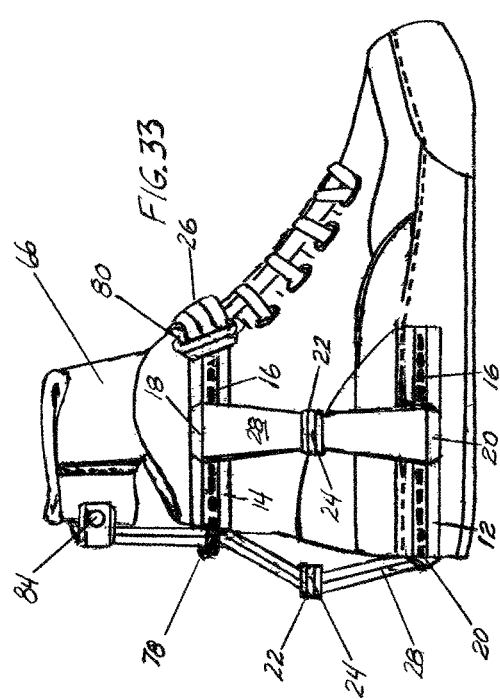
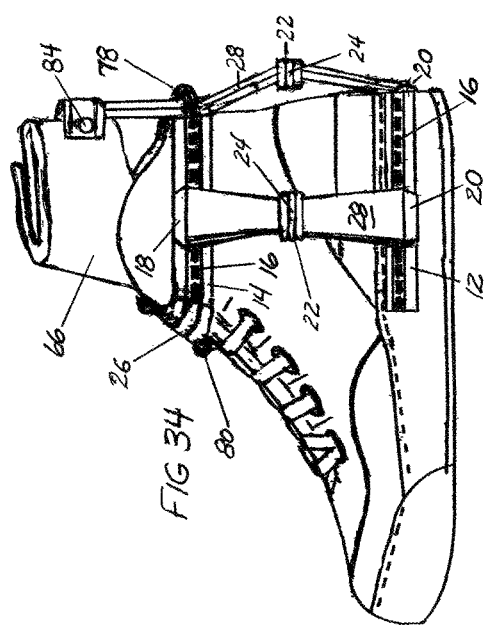

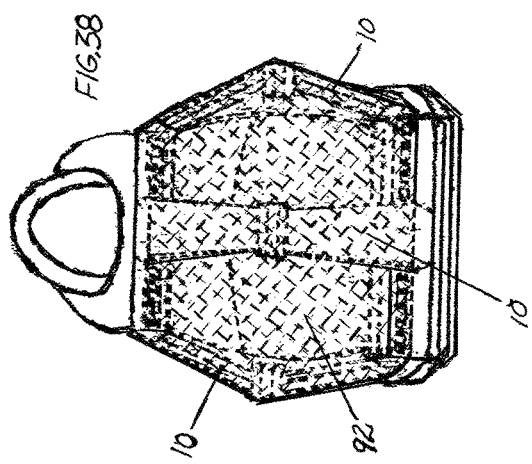
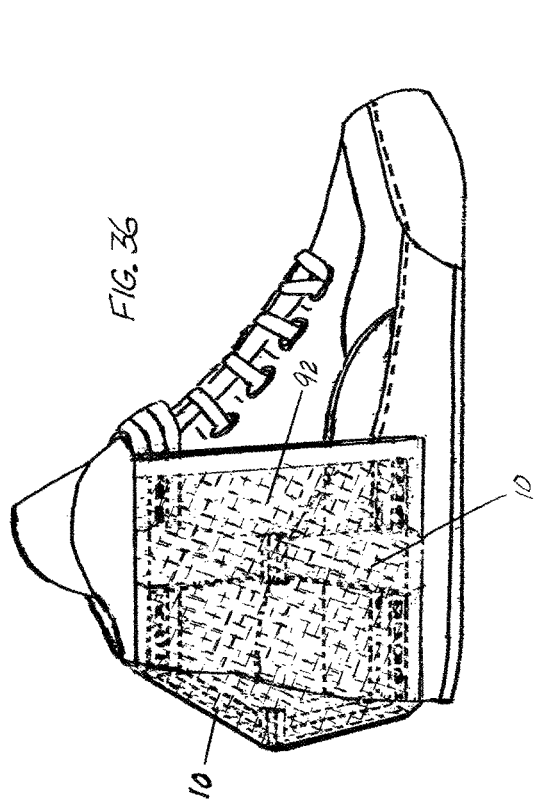
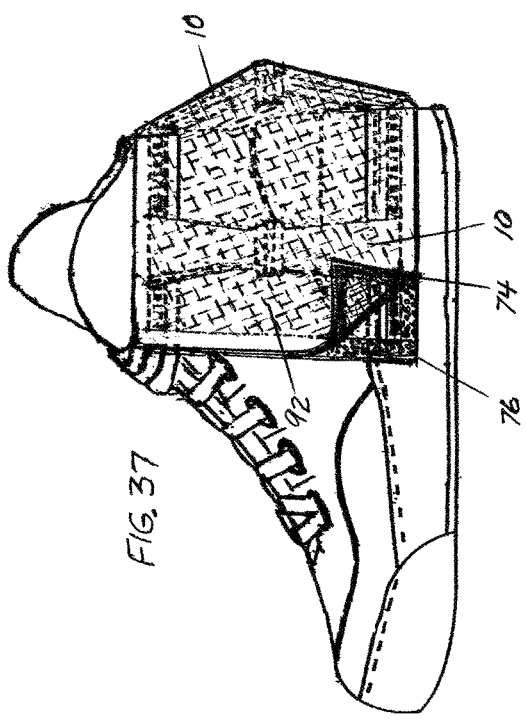

MULTI-DIRECTIONAL SUPPORT SYSTEM WITH FLEX SUPPORT BARS FOR USE ON FOOTWEAR

CROSS REFERENCE TO RELATED APPLICATIONS

This application claims the benefit of U.S. Provisional Application No. 61/897,054, filed Oct. 29, 2013.

BACKGROUND OF THE INVENTION

Field of the Invention

I have invented an improved system for multi-directional support on footwear. My invention utilizes a plurality of flex support bars adjustably positioned and mounted around the heel counter portion of the shoe, extending from on the medial side of the midfoot, around the posterior side of the heel box and to the lateral side of the midfoot.

Description of Background Art

An ankle sprain is a common injury. In sports activities, however, the injuries can be more severe as athlete's feet are subjected to constant directional forces of impact and stress. For example, when an athlete seeks to change direction and "plants" a foot, the ankle can sustain an "inversion", whereby the ankle joint moves inward as the player's body travels in the opposite direction. As the forces shift from the plant foot to the changing direction, known as "cutting", the anterior talofibular ligament, which is one of the three ligament groupings in the ankle, receives excessive stress causing an "ankle sprain". Eversion is the movement of the ankle turning outward from its natural plane. The ankle joint is subjected to outward forces when the foot remains fixed or "planted" to the surface. Such injury often occurs in basketball when players are constantly running, jumping, stopping, starting and cutting and turning in different directions and excessive forces are exerted on the structures of the feet. Injuries can also be sustained to the knees and Achilles tendon caused by misalignment of the foot as a result of insufficient support means. Athletic performance and efficiency is compromised when plagued by painful injuries that possibly can be averted through better support means to the athlete's feet.

Prior inventions have used wraps, tape, adjustable straps, splints, and braces, in devices that are worn directly on the foot. Some cannot be placed inside a shoe. And some devices replace the shoe for use in therapeutic applications and therefore cannot be used in rehab training while the athlete is participating in limited engagement of the sports activity.

"Wraps" often utilize a strap or tape comprised of various cloths or materials that is either wound around the foot in various configurations, utilizing a clip or other attaching means to secure the strap or tape to the foot. Tapes with adhesive surfaces are often used to secure a wrapping method. Wraps must be replaced often or re-wrapped due to slippage or loss of the adhesion causing the wrap to slip out of place as a result of the movement of a wearer's foot.

"Straps" have also been attached to the surface of the shoe upper or various components of the shoe by stitching, adhesives, hardware, or other attaching or mounting methods to create a wrap-like method. This method of straps also uses various materials, such as nylon or other synthetic polymers, wrapping the shoe in methods similar to a direct foot wrap or an adjustable "cinching" device, such as a buckle or other hardware closure device to secure the strap in place similar to what is accomplished by cinching a belt around a person's waist and using a buckle to secure the belt for the purpose of binding or girding. These types of straps and cinching devices have also been used in backpacks, horse saddles, casual shoes such as sandals, athletic shoes, snow shoes, snow boards, luggage and other consumer products. Unfortunately, straps also experience slippage, stretching, fraying and breakage and frequently have to be re-adjusted or replaced. Tape wraps have also been used on the foot however these devices can restrict blood flow to portions of the foot which may exacerbate the incidence of injury and affect the health and strength of the Achilles tendon which already has limited blood flow.

"Splints" and "braces" are sometimes used to immobilize a joint or bone and to entirely restrict movement. The material used for a splint or brace is usually a static rigid plate of various shapes and sizes, consisting of material such as plastic or fiberglass, and is applied directly to the affected region and usually consists of a one or more panels wrapped and secured in place. Static splints and braces are also sometimes incorporated in "rocker walkers" rehabilitative type orthopedic type appliances.

U.S. Pat. No. 1,205,206 Hofmeister describes a brace ankle protector limiting the pivotal movement of risers on the single plane for the purpose of protecting from crushing force to the ankle. U.S. Pat. No. 4,776,111 Crowley, has a stiff support and a support plate protecting the heel and achilles tendon and stiffening elements and a pivot point on one plane. U.S. Pat. No. 1,549,382 Riddell also describes a bracing means to limit pivotal movement. U.S. Pat. No. 2,972,822 Tanner describes a brace medially pivotal about an axis passing though the ankle bone and a mounting tongue portion embedded in two layers of leather which is attached to an auxiliary ankle strap or to the ankle portion of the boot with an adjustment means for lengthening the braces. U.S. Pat. No. 3,834,377 Lebold describes another type of brace, a removable orthopedic shoe platform for patients having partial paralysis or "foot drop", incorporating rigid ankle supporting members and straps with hook and loop fasteners. U.S. Pat. No. 4,766,681 O'Rourke et al. describes joining lateral and medial sheet Y shape spring portions to substantially form the upper, constructed of material that resists twisting out of its plane or deflection from its axis, bends, but does not stretch or compress. U.S. Pat. No. 5,056,509 Swearington describes an ankle brace with a foot plate worn within an athletic shoe, flexible inner brace and rigid outer brace, hinged with a U-shaped upper portion engaging the ankle. U.S. Pat. No. 4,977,891 Grim, describes insertion into a shoe of an ankle brace having two relatively rigid side supports with inflatable bladders attached to them with side supports held in place about the lower leg and ankle by straps. U.S. Pat. No. 5,771,608 Peterson describes a shoe with ankle strap protector with adjustable buckle members and fixed length side straps extending from the ankle strap, though slots disposed through the upper along each side of the shoe to provide a stirrup-like arrangement. U.S. Pat. No. 3,613,273 Marquis describes an ankle support to the outside of the wearer's leg to bias the outer edge of the foot upwardly after activities such as jumping, with adjustable length elastic members connected to an ankle strap to adjust its tension if it stretches permanently. U.S. Pat. No. 4,922,630 Robinson describes an inversion only resisting device which allows the ankle unrestricted range of motion in all planes and directions except inversion and utilizes an adjustable length leg engaging strap with a piece of elastic material or gore to restore the foot to a supinated position. U.S. Pat. No. 4,989,350 Bunch et al. describes using sheet springs forming a strut unaffixed to the upper to give the wearer's ankle leeway to flex forward and rearward but restrains the ankle from flexing laterally or medially, unstretchable and incompressible, made of material resistant to bending and twisting out of its plane. U.S. Pat. No. 5,672,156 Jimenez Ramos describes a device to avoid twists in ankles with a strap around the superior part of the ankle, pivotally joined to a removable rigid or semi-rigid sheet shaped or bent to accommodate the contours of the ankle bone, with an end inserted in a little box but not attached there, the sheet does not allow bending when an excessive movement is committed. U.S. Pat. No. 2,634,515 Saitta describes a shoe to prevent lateral flexing or twisting of the shoe or foot with a plurality of spaced substantially inflexible ribs secured in pockets between the upper and lining. U.S. Pat. No. 5,430,960 Richardson describes a lightweight athletic shoe with foot and ankle support systems with a brace attached to the upper, removable ankle support elements and a comfort system with air pockets in the upper. U.S. Pat. No. 5,896,683 Foxen et al. describes inversion/eversion limiting support using a plurality of finger-like elements, on the medial and lateral sides of an article of footwear, with a shape to conform to the contour of the ankle region of the upper and a breadth extending a distance generally away from the upper or secured to the upper and extending vertically upward from the sole along the upper at the forefoot, midfoot, and rearfoot, so the element will bend freely in the dorsi and plantar flexion plane and not in the medial and lateral flexion plane. U.S. Pat. No. 5,152,082 Culpepper describes a shoe and ankle support therefore, the ankle support member a stiff resilient piece of bendable sheet material including a base portion and a plurality of lateral and medial strips, U-shaped base portion extending behind the heel and bonded to the sole, at least one of the lateral strips connected together in a rear part of the shoe forming an inverted loop, the lateral and medial strips having free upper ends curved toward each other to deter lateral movement of the ankle, with an ankle support member frame built into the shoe, formed of a single piece of sheet material. U.S. Pat. No. 6,715,218 Johnson describes a unidirectional support device with exoskeleton and spine disposed on the medial, lateral, or posterior sides, stitched to or bonded to the upper, or by a hook and loop fastener, manufactured by injection molding or extrusion, substantially flexible in one direction while substantially rigid in an opposing direction for preventing injury to flexural joints of the foot, knee, elbow, neck, shoulder, hip, hand and fingers. U.S. Pat. No. 5,125,171 Stewart describes a shoe with spring biased upper for biasing the upper in the plantar flexion position by storing potential energy to urge the shoe toward the plantar flexion position after the shoe is moved to the dorsiflexion position, to assist the user in jumping, with a bowed resilient rod made of resilient material extending along the sagitall plane from the ankle region to the forefoot. U.S. Pat. No. 7,171,766 Bouche et al. describes an ankle and foot stabilization support foundation to be removably fastened to a leg of a user at a point above the ankle, which can be moved from footwear to footwear, to provide support in the neutral and dorsiflexed position with lateral and medial adjustable tension bands which slideably engage to an attachment member to the article of footwear by slot, grommet, ring or opening through which a tension band passes.

The prior art shows many different types of devices with various combinations of straps, wraps, braces, stirrups, and splints which can be worn inside a shoe, attached to an article of footwear, partially attached to a an article of footwear and partially attached to the foot, or even devices that can be entirely removed and worn interchangeably on a different shoe. Other prior art inventions describe unidirectional support devices or hinged devices or static braces stitched to or bonded to the upper. Many of the parts used in the prior art devices include parts such as gore, adjustable straps, pockets inside the upper, between the upper and lining, or on the upper to hold rigid plates, braces, ribs, unstretchable and incompressible sheets, and even rods extending along the sagittal plane from the heel to the forefoot. Some of these prior art devices use parts which may unintendedly impair or impede other basic and complex movements of the foot and ankle and even lead to stress related injury, such as devices flexible in a single plane only, when the human foot must move naturally on multiple planes and in multiple directions. For example, a device with a flexible rod or spring extending from the heel to forefoot, to assist and provide stability when jumping may actually impair or impede a natural running motion in the dorsi and plantar flexion sagittal plane, because of the additional resistance caused by the rod or spring that could slow down the wearer while engaging in sport or even result in overcompensation and stress related injury to small bones in the foot such as the fifth metatarsal bone. Also the use of an rigid sheet or brace that does not allow bending when an excessive movement is committed becomes counter-productive to providing precision support complimentary to the complex bony structure of the foot as it is engaged in movement in sports activities. Some of the prior art devices use air brace stirrups or air pockets for comfort within the shoe upper for the purpose of providing a brace or a comfort layer between the brace and the foot. Therefore, many of the inventions of the prior art are cumbersome in use and contemplate solving one support related problem but ignore several limitations or impediments inherently caused by the devices.

Many of the prior art inventions also utilize parts that can easily become worn or compromised such as hinges or strap materials or elastic materials that may permanently become stretched, fabric pockets housing rigid plates or parts that can be prone to wear and become unattached during the wearer's activities, or parts like a pivotally attached, unbendable sheet with an end inserted into a little box but not attached there which may become worn by frictional engagement and movement of the two parts or become entirely displaced with a sudden movement or counter force and could result in tripping or potentially, a serious injury. Several prior art inventions describe braces such as fingerlike elements attached directly to the upper by various means or are attached only on one end, leading to the potential of the part causing wear on the upper and eventually even having the potential to pierce the upper and impale the wearer's foot. Other support devices of the prior art require constantly re-adjusting or engaging multiple straps by use of buckles or hook and loop type fasteners which may become unfastened, and as such, are not only inconvenient and may be unsuited for certain types of competitive sporting game activities such as basketball.

The devices of the prior art, while providing some support means, are limited in versatility and both the function and direction of the support provided by the device. For example, much of the prior art provides support only on a single plane, such as by the use of hinged risers or braces, which permit pivotal movement in one direction but entirely restricts movement in another direction. Also, many of the devices of the prior art utilize the cinching of a strap to create tension, only to create a limited buttressing effect similar to the attachment of strips or Y shaped spring portions attached to or bonded on the lateral or medial sides, joining together in a single piece and surrounding the posterior side of the heel, similar to a heel counter. Further, the cinching motion of adjusting straps exerts force in the same direction in which the strap is pulled and therefore affords limited counter resistance and in some cases tends to pull away from the attachment point or crimp the upper rather than to apply directional support at the attachment point. The use of air in some of the devices of the prior art are for static inflated braces or cushioning that are not similar to and do not anticipate the use of air, gas, liquid gel, or other resilient filler material to induce dynamic pressure-flexed support bars which are alternate described embodiments in this specification.

The prior art devices also cannot be easily adjusted along the horizontal plane of the foot or to precise positions to impart direct support on the medial, lateral, and posterior sides. Also, the prior art devices lack the precise multi-directional support or capability to provide tandem support in multiple planes and multiple directions.

SUMMARY OF THE INVENTION

A Support Bar 10 can be straight, angular, semi-curved or other shape or combination. Support Bar 10 is referenced generically throughout portions of this specification to facilitate the understanding of how my invention functions and achieves its results. Other types of support bar constructions are also referenced in more detail. As utilized in my invention, the Support Bar 10 is "flexed" similar to the stringing of a bow and similar to a bow has "limb" portions that extend from the center portion of the Support Bar 10 to its ends. Flexing the Support Bar 10 enables energy to be transferred into the Support Bar 10 creating a spring-type action when flexing tension is applied and the Collar Mounting End 18 and Base Mounting End 20 is mounted in a tensioned "bow-like" manner to the shoe. When the potential energy of the flexing spring tension is released the Support Bar 10 returns to its original shape and the energy is responsible for returning a restoring force to support and counter excessive ranges of foot eversion and inversion, or excessive pronation or supination.

Hooke's law is a principle of physics that states that the force F needed to extend or compress a spring by some distance X is proportional to that distance. That is, F=kx where k is a constant factor characteristic of the spring, its "stiffness".

The spring of the flex support bars are not to be stretched or compressed beyond their elastic limits, i.e. the "spring" of the support bars generally obey Hooke's law within their elastic limits.

F=k x d
F=force applied on the spring
k=spring rate
d=displacement

Also Hooke's Law is used to measure the stored energy of the spring equivalent rate K eq when multiple support bars with different spring "stiffness" are used in parallel configuration.

1/k eq=1/k 1+1/k 2 . . . 1/k n, where n is the number of springs

The equivalent displacement, d is given by:

d=d 1=d 2 . . . d n, where n is the number of springs

In my invention, a plurality of pressure-flexed support bars of varying types are adjustably positioned and mounted around the heel box portion of the shoe on the medial side, lateral side, and the posterior Achilles side of the heel box to provide multi-directional support. The varying types of support bars provide for versatility in combining their use so as to maximize support for different types of footwear as well as sports activities.

The different materials used for construction of and the different types of flex support bars can be adapted for use based on the type of footwear applications, the wearer's weight, as well as the type of sports activity to help ensure that the selected support bars do not exceed their elastic limits during use. Various types of support bars can also be used and interchanged during sports training and rehab to provide varying levels of progressive support intensity and resistance.

Various aspects of my Multi-Directional Support System With Flex Support Bars For Use On Footwear invention may have one or more of the following advantages.

One advantage is that support bars can be adapted to and adjusted for a variety of footwear types and user support requirements including sports activities.

Another advantage is greater versatility and a range of adjustable support options to various parts of the foot.

Another advantage is reducing breakdown of the shoe components structure by increasing the stability of the shoe.

Another advantage is increasing shoe comfort by providing additional support and a more secure fit.

Another advantage is greater control of the foot's range of motion.

Another advantage of is to increase medial, lateral and posterior multi-directional support to the foot when the shoe is subject to the forces of torque, flex-stress, and g-force while walking, running, or engaging in other sports activities including basketball and football.

Another advantage is to reduce stress causing foot strains and fractures caused by excessive range of motion by providing increased concerted biomechanical support to the structure of the foot during motion related activities.

Another advantage is to help keep the foot in a more neutral alignment and control and limit excessive range of motions including inversion and eversion, and excessive pronation and supination.

Another advantage of is to help reduce the incidence and severity of injuries to the foot, particularly to the ankle region where strains and tearing of tendons such as the Achilles and adjoining ligaments, by displacing forces of stress into the tensile strengthened support bar components thereby helping to reinforce and protect the tensile strength of tendons and ligaments.

Another advantage is providing additional footwear support adjustment options during rehabilitation and therapy of foot related injuries, including sprains, torn ligaments and tendons.

Another advantage is additional stability and greater support to the shoe structure and reducing the incidence and severity of damage to the ankles and knees caused by excessive foot range of motion affecting the planar alignment of the foot and the tibia/fibula during high impact sports activities in which participants are repeatedly starting, stopping, pivoting, cutting and turning in which the shoe's sole surface may partially lose stable contact with the floor or ground.

Another advantage is to help control the range of motion by providing additional support to the medial and lateral sides of the foot.

Another advantage is to help reduce the stress and strain on the Achilles tendon.

DESCRIPTION OF THE DRAWINGS

FIG. 1 shows the medial side view of a basketball shoe.
FIG. 2 shows the lateral side view of a basketball shoe.
FIG. 3 is a posterior heel view of a basketball shoe.
FIG. 4 shows the medial side view of a basketball shoe.
FIG. 5 shows the lateral side view of a basketball shoe.
FIG. 6 is a posterior heel view of a basketball shoe.
FIG. 7 shows the medial side view of a basketball shoe.
FIG. 8 shows the lateral side view of a basketball shoe
FIG. 9 is a posterior heel view of a basketball shoe.
FIG. 10 shows the medial side view of a basketball shoe.
FIG. 11 shows a lateral side view of a basketball shoe.
FIG. 16 shows a side view of a partially flexed bladder type support bar.
FIG. 17 is a side view of a partially flexed bladder type support bar.
FIG. 18 is a vertical face view of an un-flexed bladder type support bar.
FIG. 19 shows a vertical face view an un-flexed blade type support bar.
FIG. 20 shows a vertical face view of an un-flexed blade type support bar.
FIG. 21 shows a vertical face view of a pre-flexed support bar.
FIG. 22 is a vertical view of the face of an un-flexed support bar.
FIG. 23 shows a vertical face view of an un-flexed support bar.
FIG. 24 shows an exploded and cross-sectional view of a stud bolts track strip.
FIG. 25 shows an exploded and cross-sectional view of a slot hooks track strip.
FIG. 28 is a perspective view of the midsole.
FIG. 29 shows an overhead view of the base track midsole insert.
FIG. 30 shows a heel side view of the base track midsole insert.
FIG. 31 shows a medial side view of the base track midsole insert.
FIG. 32 shows a posterior angle view of a basketball shoe.
FIG. 33 is a medial side view of a basketball shoe.
FIG. 34 shows a lateral side view of a basketball shoe.
FIG. 35 is a posterior heel side view of a basketball shoe.
FIG. 36 shows the medial side view of a basketball shoe.
FIG. 37 shows the lateral side view of a basketball shoe.
FIG. 38 is a rear heel view of a basketball shoe.

DETAILED DESCRIPTION OF THE INVENTION

Figure 12:
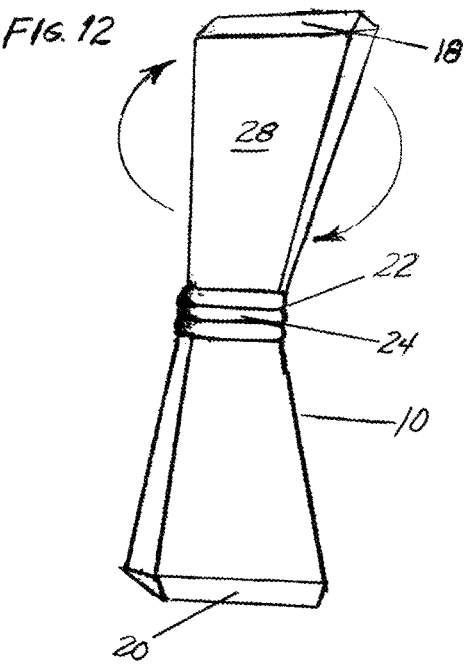
FIG. 12 is a vertical face view of an un-flexed bladder type support bar.

FIG. 1 shows the medial side view of a basketball shoe showing flexed removable Support Bar 10 with the Collar Mounting End 18 adjustably mounted on the Slots Track Strip 16 of Collar Track 14 and aligned semi-perpendicular to Collar Track 14 on the shoe upper with the distal Base Mounting End 20 of Support Bar 10 mounted to the Slots Track Strip 16 on Base Track 12 protruding from the insertion in the midsole of the shoe. Shown on the heel portion of the shoe is a second Support Bar 10 with a similar mounting on the Collar Track 14 and Base Track 12 illustrating the distance of the bowed Flex Point 22 from the heel portion of the shoe upper. Each flexed Support Bar 10 shown has Ribs 24 on the Flex Point 22. Aligned on and attached to the Collar Track 14 is Cinch Ring 80 used with the Collar Closure Strap 26.

FIG. 2 shows the lateral side view of a basketball shoe showing flexed removable Support Bar 10 with the Collar Mounting End 18 adjustably mounted to the Slots Track Strip 16 on Collar Track 14 and aligned vertically semi-perpendicular to Collar Track 14 on the shoe upper with the distal Base Mounting End 20 of Support Bar 10 mounted to the Slots Track Strip 16 on Base Track 12 protruding from the insertion in the midsole of the shoe. Shown on the heel portion of the shoe is a second Support Bar 10 with a similar mounting on the Collar Track 14 and Base Track 12. Each flexed Support Bar 10 shown has Ribs 24 on the Flex Point 22. Aligned on and attached to the Collar Track 14 is Cinch Ring 80 used with the Collar Closure Strap 26. Also shown is an "open" Strap Closure Strap 26 with Loops 76 and Hooks 74 threaded through the Cinch Ring 80 attached to the Collar Track 14.

FIG. 3 is a posterior heel view of a basketball shoe showing flexed removable Support Bar 10 with the Collar Mounting End 18 adjustably mounted to the Slots Track Strip 16 on Collar Track 14 and aligned vertically semi-perpendicular to Collar Track 14 on the shoe upper with the distal Base Mounting End 20 of Support Bar 10 mounted to the Slots Track Strip 16 on Base Track 12 protruding from the insertion in the midsole of the shoe. Each flexed Support Bar 10 shown has Ribs 24 on the Flex Point 22. Shown on the medial and lateral sides of the heel portion of the shoe is, respectively, a second and third Support Bar 10 with a similar mounting on the Collar Track 14 and Base Track 12 and demonstrating the distance of the bowed Flex Point 22 from the shoe upper on the medial and lateral sides.

FIG. 4 is the medial side view of a basketball shoe showing flexed removable Bladder Type Support Bar 28 with Collar Mounting End 18 adjustably mounted to the Slots Track Strip 16 on Collar Track 14 and aligned vertically semi-perpendicular to the Collar Track 14 on the shoe upper with the distal Base Mounting End 20 of the Bladder Type Support Bar 28 mounted to the Slots Track Strip 16 on Base Track 12 protruding from the insertion point in the layer between the shoe upper and midsole. Shown on the heel portion of the shoe is a second Bladder Support Bar 28 with a similar mounting on the Collar Track 14 and Base Track 12. Each flexed Bladder Type Support Bar 28 shown has Ribs 24 on the Flex Point 22. Aligned on and attached to the Collar Track 14 is Cinch Ring 80 used with the Collar Closure Strap 26.

FIG. 5 is the lateral side view of a basketball shoe showing flexed removable Bladder Type Support Bar 28 with Collar Mounting End 18 adjustably mounted to the Slots Track Strip 16 on Collar Track 14 and aligned semi-perpendicular to Collar Track 14 on the shoe upper with the distal Base Mounting End 20 of the Bladder Type Support Bar 28 mounted to the Slots Track Strip 16 on Base Track 12 protruding from the insertion point in the layer between the shoe upper and midsole. Shown on the heel portion of the shoe is a second Bladder Type Support Bar 28 with a similar mounting on the Collar Track 14 and Base Track 12. Each flexed Bladder Type Support Bar 28 shown has Ribs 24 on the Flex Point 22. Aligned on and attached to the Collar Track 14 is Cinch Ring 80 used with the Collar Closure Strap 26. Also shown is a "closed" hook and loop Collar Closure Strap 26 threaded through the Cinch Ring 80 on the Collar Closure Strap 26 attached to the Collar Track 14.

FIG. 6 is a posterior heel view of a basketball shoe showing flexed removable Bladder Type Support Bar 28 with Collar Mounting End 18 adjustably mounted to the Slots Track Strip 16 on Collar Track 14 and aligned semi-perpendicular to Collar Track 14 on the shoe upper with the distal Base Mounting End 20 of the Bladder Type Support Bar 28 adjustably mounted to the Slots Track Strip 16 on Base Track 12 protruding from the insertion point in the layer between the shoe upper and midsole. Each flexed Bladder Type Support Bar 28 shown has Ribs 24 on the Flex Point 22. Shown on the medial and lateral sides of the heel portion of the shoe is a second and third Bladder Type Support Bar 28 with a similar mounting on the Collar Track 14 and Base Track 12 and demonstrating the distance of the bowed Flex Point 22 from the shoe upper on the medial and lateral sides.

FIG. 7 is the medial side view of a basketball shoe showing flexed removable Blade Type Support Bar 30 with the Collar Mounting End 18 adjustably mounted to the Slots Track Strip 16 on Collar Track 14 and aligned semi-perpendicular to Collar Track 14 on the shoe upper with the distal Base Mounting End 20 of the Blade Type Support Bar 30 adjustably mounted to the Slots Track Strip 16 on Base Track 12 protruding from the insertion point in the layer between the shoe upper and midsole. Shown on the medial side of the shoe is a second Blade Type Support Bar 30 with varying shapes and angles demonstrating that multiple support bars of different types can also be mounted in close proximity for additional support. On the heel portion of the shoe is a Blade Type Support Bar 30 with a similar mounting on the Collar Track 14 and Base Track 12. Each flexed Blade Type Support Bar 30 shown has Ribs 24 on the Flex Point 22. Aligned on and attached to the Collar Track 14 is Cinch Ring 80 used with a Collar Closure Strap 26.

FIG. 8 shows the lateral side view of a basketball shoe showing flexed removable Blade Type Support Bar 30 with the Collar Mounting End 18 adjustably mounted to the Slots Track Strip 16 on Collar Track 14 and aligned vertically semi-perpendicular to Collar Track 14 on the shoe upper with the distal Base Mounting End 20 of the Blade Type Support Bar 30 adjustably mounted to the Slots Track Strip 16 on Base Track 12 protruding from the insertion point in the layer between the shoe upper and midsole. Also shown is a lateral side Blade Type Support Bar 30 with a Flex Point 22 with a position height which is lower compared to the other Flex Point 22 heights on the other support bars demonstrating the use of Flex Point 22 height positioning to influence force directional movement. Shown on the heel portion of the shoe is a second Blade Type Support Bar 30 with a similar mounting on the Collar Track 14 and Base Track 12. Each flexed Blade Type Support Bar 30 shown has Ribs 24 on the Flex Point 22.

FIG. 9 is a posterior heel view of a basketball shoe showing flexed removable Blade Type Support Bar 30 with the Collar Mounting End 18 adjustably mounted to the Slots Track Strip 16 on Collar Track 14 and aligned semi-perpendicular to the Collar Track 14 on the shoe upper with the distal Base Mounting End 20 of the Blade Type Support Bar 30 adjustably mounted to the Slots Track Strip 16 on Base Track 12 protruding from the insertion point in the layer between the shoe upper and midsole. As shown, the Blade Type Support Bar 30 positioned on the Achilles portion of the heel has an Achilles "Y" Notch 32 cutout. Each flexed Blade Type Support Bar 30 shown has Ribs 24 on the Flex Point 22. Shown on the medial and lateral sides of the heel portion of the shoe is a overlapping view of the second and third Blade Type Support Bar 30 on the medial side and a fourth Blade Type Support Bar 30 on the lateral side with a similar mounting on the Collar Track 14 and Base Track 12 and demonstrating the distances of the bowed Flex Point 22 from the shoe upper on the medial and lateral sides.

FIG. 10 is the medial side view of a basketball shoe showing flexed removable Blade Type Support Bar 30 with the Collar Mounting End 18 adjustably mounted to the Slots Track Strip 16 on the Collar Track 14 and aligned vertically perpendicular to the Collar Track 14 on the shoe upper with the distal end of the Blade Type Support Bar 30 with the Base Mounting End 20 mounted to the Slots Track Strip 16 on Base Track 12 protruding from the insertion in the midsole of the shoe. As shown, the Blade Type Support Bar 30 is also mounted on the rear heel Achilles portion of the shoe. A straight "un-flexed" Blade Type Support Bar 30 with Flex Point 22, is also shown in the diagram, to illustrate the varying angle and direction of mounting flex pressure necessary, similar to the stringing of a bow whereby a constant directional pressure is created and stored, which can be measured in pounds. Through the use of single or multiple support bars mounted on the medial side, lateral side and posterior heel, the stored pressure is distributed multi-directionally, illustrating force and resistance exerted on the Flex Point 22 as well as on the limb ends where the Blade Type Support Bar 30 is mounted to the Collar Track 14 as well as the distal end of the Blade Type Support Bar 30 mounted to the Slots Track Strip 16 on Base Track 12.

FIG. 11 is a lateral side view of a basketball shoe showing removable Bladder Type Support Bar 28 with the Collar Mounting End 18 adjustably mounted to the Slots Track Strip 16 on Collar Track 14 and aligned vertically perpendicular to Collar Track 14 on the shoe upper with the distal Base Mounting End 20 of the Bladder Type Support Bar 28 mounted to the Slots Track Strip 16 on Base Track 12 which is inserted in the midsole of the shoe. As shown, the Bladder Type Support Bar 28 mounted on the posterior heel Achilles portion of the shoe can be pressure injected and filled with air, gas, gel, pellets or other material and illustrates expandable and stretchable Ribs 22 at Flex Point 22, illustrating the varying angle and direction of flex similar to the stringing of a bow whereby a constant directional pressure is created and stored, which can be measured in pounds. Through the use of single or multiple support bars, the stored pressure is distributed multi-directionally, exerting force on the Ribs 24 at Flex Point 22 as well as exerting force on the limb ends where the Bladder Type Support Bar 28 is mounted to the Collar Track 14 and force on the distal end of the Bladder Type Support Bar 28 mounted to the Base Track 12.

FIG. 12 is a vertical face view of an un-flexed Bladder Type Support Bar 28, illustrating flexibility and directional twisting when a torque force is applied, in which the Ribs 24 at Flex Point 22 enables the upper portion of the Bladder Type Support Bar 28 illustrating a range of twisting motion resistance. The Bladder Type Support Bar 28 also shows a Collar Mounting End 18 and a Base Mounting End 20 on the limbs extending from the Flex Point 22.

Figure 13:
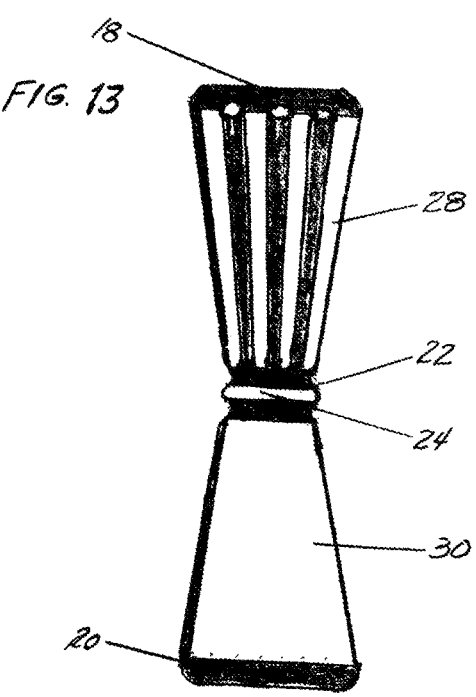
FIG. 13 is a vertical view of the face of an un-flexed combination type support bar.

FIG. 13 is a vertical view of the face of an un-flexed combination type support bar, illustrating a ribbed pressure injected upper limb portion Bladder Type Support Bar 28 construction, filled with air, gas, gel, pellets or other material extending from the Flex Point 22 to the upper limb end. The lower limb portion illustrates a Blade Type Support Bar 30 construction of a solid flexible material, extending from the Flex point 22 to the lower limb end. Also shown is a Collar Mounting End 18 on the Bladder Type Support Bar 28 construction upper limb that extends from the Flex Point 22 and a Base Mounting End 20 on the Blade Type Support Bar 30 construction lower limb extending from the Flex Point 22.

Figure 14:
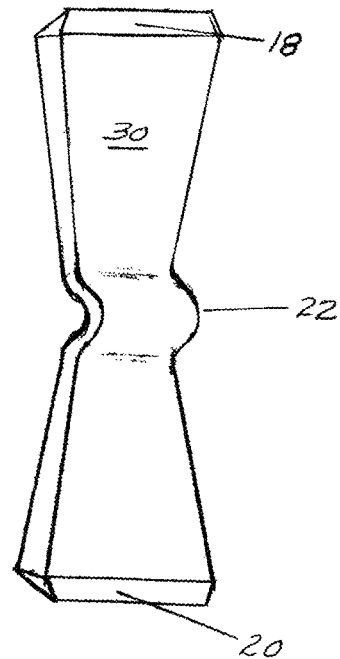
FIG. 14 shows a vertical view of the face of an un-flexed blade type support bar.

FIG. 14 shows a vertical view of the face of an un-flexed Blade Type Support Bar 30, illustrating a solid flexible material blade construction including a rounded, face-protruding Flex Point 22. The Blade Type Support Bar 30 also shows a Collar Mounting End 18 and a Base Mounting End 20 on the limbs extending from the Flex Point 22.

Figure 15:
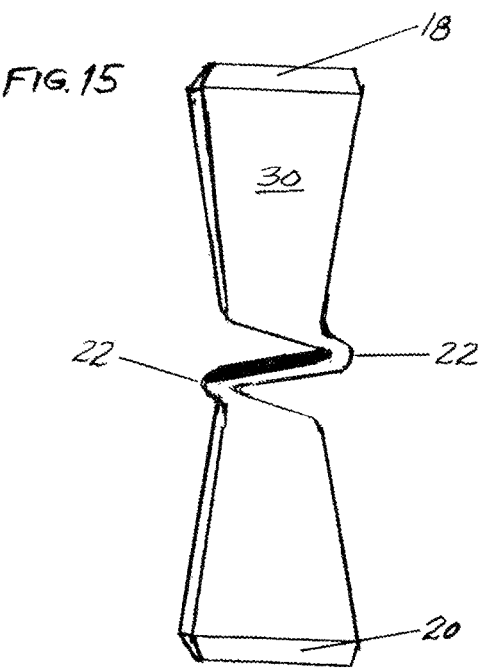
FIG. 15 shows a vertical view of the face of an un-flexed blade type support bar.

FIG. 15 shows a vertical view of the face of an un-flexed Blade Type Support Bar 30, illustrating a solid flexible material blade construction including a z-shaped type spring with tandem Flex Point 22. The Blade Type Support Bar 30 also shows a Collar Mounting End 18 and a Base Mounting End 20 on the limbs extending from the Flex Point 22.

FIG. 16 shows a side view of a partially flexed Bladder Type Support Bar 28, illustrating a construction of the bladder inflated or injected with air, gas, gel, pellets or other material including a Flex Point 22 with elastic and expandable Ribs 24. A Slot Hook 60 is shown on the Collar Mounting End 18 of the Bladder Type Support Bar 28 and a Slot Hook 60 is also shown on the distal Base Mounting End 20. The Bladder Type Support Bar 24 has a Slot Hook 60 on each limb end for attachment means to the Slots Track Strip 16 on the Collar Track 14 and the Base Track 12 (which are not show on this drawing figure). Illustrated are an Insertion Needle 34 and a Bladder Valve 36 for inflating, filling, or injecting the Bladder Type Support Bar 28 with air, gas, gel, pellets or other filler material. Also illustrated are the flexing directions of the upper limb portion of the Bladder Type Support Bar 28 and the lower limb portion of the Bladder Type Support Bar 28 when the Flex Point 22 enables directional compression. As illustrated, the flex angle measurable from the Flex Point 22 to the top limb end of the Bladder Type Support Bar 28 is in a range of more than 90 degrees when flexed and equal to or less than 180 degrees when fully extended and un-flexed, and the flex angle measureable from the Flex Point 22 to the bottom limb end of the Bladder Type Support Bar 28 is in a range of less than 90 degrees to equal to or less than 0 degrees when fully extended and un-flexed. Optimal flex is at a range of 150 degrees to 165 degrees for the top limb portion of the Bladder Type Support Bar 28 and 15 degrees to 30 degrees for the bottom limb portion of the Bladder Type Support Bar 28, although different angles can be employed for the top and bottom limbs.

FIG. 17 is a side view of a partially flexed Bladder Type Support Bar 28, illustrating a molded, sealed and welded construction, filled or injected with pellets or other Bladder Filler Material 40, showing expandable Ribs 24 at Flex Point 22. As shown, the upper limb end of the Bladder Type Support Bar 28 has a Weld 38 adjacent to the Collar Mounting End 18 as does the lower limb end of the Support Bar 28 also show a Weld 38 adjacent to Base Mounting End 20. A Slot Hook 60 is shown on the Collar Mounting End 18 of the Bladder Type Support Bar 28 and a Slot Hook 60 is also shown on the distal Base Mounting End 20. Also illustrated is an enlarged exploded view showing pellets or other shaped Bladder Filler Material 40 such as cell-closed polystyrene foam filling the Bladder Type Support Bar 28.

FIG. 18 is a vertical face view of an un-flexed Bladder Type Support Bar 28, illustrating an enlarged exploded view showing the directional expansion of Ribs 24 at the Flex Point 22 and demonstrating flexibility, resistance and elastic stretching properties. The Bladder Type Support Bar 28 also shows a Collar Mounting End 18 and a Base Mounting End 20 on the limbs extending from the Flex Point 22.

FIG. 19 shows a vertical face view an un-flexed Blade Type Support Bar 30 for the posterior heel of a shoe to adjustably attach to the Slots Track Strip 16 on the Collar Track 14 and aligned vertically semi-perpendicular to the Collar Track 14 on the shoe upper with the distal ends of the Blade Type Support Bar 30 adjustably mounted to the Slots Track Strip 16 on the Base Track 12. Slots Track Strip 16, Collar Track 14, and Base Track 14 are shown in FIG. 9. As shown, the Blade Type Support Bar 30 for attaching on the posterior Achilles portion of the heel has an Achilles "Y" Notch 32 cutout shape where the Blade Type Support Bar 30 attaches to the Slots Track Strip 16 on the Collar Track 14 or Base Track 12. As shown, the Blade Type Support Bar 30 has a series of varying width and expansive and elastic Flex Point 22 portions with Ribs 24 for varying resistance, support and shock absorption. A Collar Mounting End 18 is shown on each limb of the "Y" section on the upper limb extending from the upper series of Flex Point 22 sections and a Base Mounting End 20 on the lower limb extending from the lower Flex Point 22.

FIG. 20 shows a vertical face view of an un-flexed Blade Type Support Bar 30, illustrating a series of structural horizontal Cutout 42 with the cutouts extending from the Ribs 24 of the Flex Point 22 to the Collar Mounting End 18 on the upper limb and extending from Flex Point 22 to the Base Mounting End 20 on the lower limb of the Blade Type Support Bar 30.

FIG. 21 shows a vertical face view of a pre-flexed Support Bar 10, illustrating a Support Bar 10 in which the Ribs 24 of the Flex Point 22 protrude from the attached Support Bar Frame 44 in which the stitched portion of the Support Bar Frame 44 positions and attaches the Support Bar 10 to the shoe upper and keeps it in place. The Support Bar Frame 44 can be used for either for either a solid blade type Support Bar 10 or for a bladder type support bar. The Support Bar 10 is stitched to the Support Bar Frame 44 at the Collar Mounting End 18 at the Base Mounting End 20. Alternatively, buttons, rivets, hook and loop or other attachment means may be utilized for attaching a removable Support Bar Frame 44 to the shoe upper or for attaching a removable Support Bar 10 to the Support Bar Frame 44 and to afford adjustable positioning.

FIG. 22 is a vertical view of the face of an un-flexed Support Bar 10, illustrating a series of geometric Cutout 42 for either a solid blade type or bladder type Support Bar 10, with the cutouts extending from the Ribs 24 of the Flex Point 22 to the Collar Mounting End 18 on the upper limb and extending from Flex Point 22 to the Base Mounting End 20 on the lower limb of the Support Bar 10.

FIG. 23 shows a vertical face view of an un-flexed Support Bar 10, with Ribs 24 at the Flex Point 22, and illustrates a Dual Ring Connector 46 on the Collar Mounting End 18 and a Dual Ring Connector 46 on the Base Mounting End 20 used for aligning and bolting the Support Bar 10 in place on the on stud bolts of the Stud Bolts Track Strip 50 as show on FIG. 24. Also illustrated is a Weld 38 on a molded and sealed construction on the upper limb adjacent to the Collar Mounting End 18 and on the lower limb adjacent to the Base Mounting End 20 of the Support Bar 10.

FIG. 24 shows an exploded and cross-sectional view of a Stud Bolts Track Strip 50 mounted onto a Slide-on Track 58, illustrating a Support Bar 10 with Ribs 24 at the Flex Point 22 and with Dual Ring Connector 46 to attach on two different threaded Stud Bolt 52 on the Stud Bolt Track Strip 50, and secured by two threaded nuts, either standard Driver Head Nut 54 or Hex Nut 56. As shown, the Support Bar 10 shows the Collar Mounting End 18. Alternatively, the attachment can be made by convenient threaded wing nuts secured to threaded Stud Bolt 52 and the same configuration method can be used for the Base Mounting End 20 of the Support Bar 10, which is not shown in this drawing.

FIG. 25 shows an exploded and cross-sectional view of a Slot Hooks Track Strip 86 mounted onto a Slide-on Track 58, illustrating a Support Bar 10 with Ribs 24 at the Flex Point 22 and with Slot Hook 60 to attach on the selected Slot 61. As shown, the Support Bar 10 shows the Collar Mounting End 18. Alternatively, the same configuration method can be used for the Base Mounting End 20 of the Support Bar 10, which is not shown in this drawing.

Figure 26:
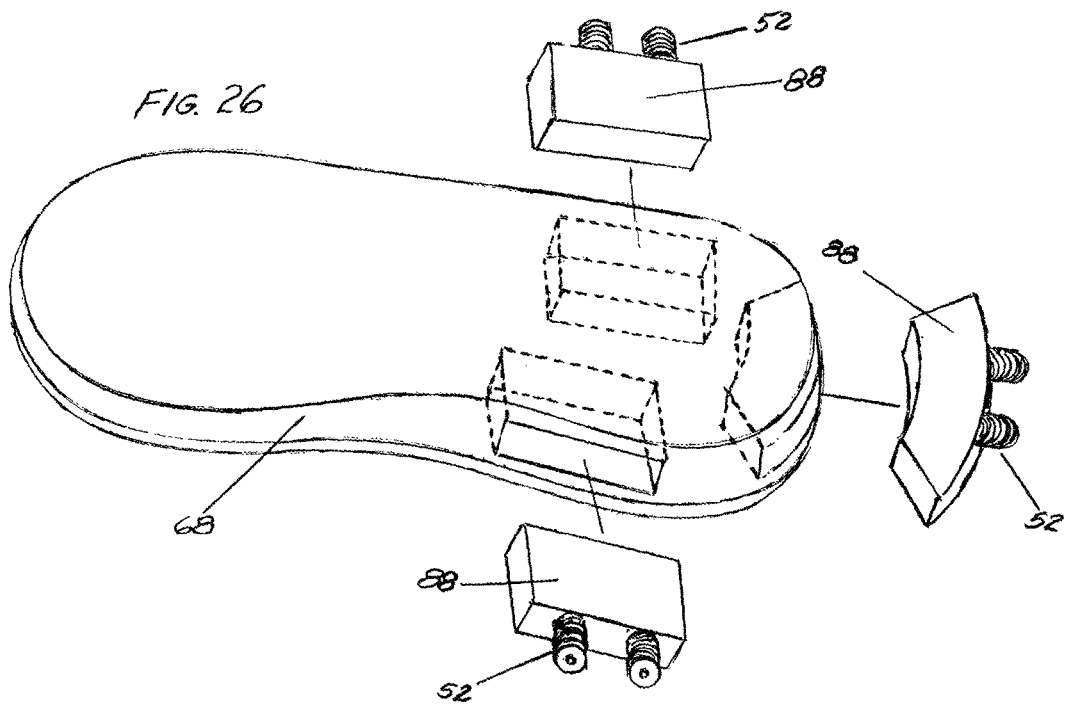
FIG. 26 is a perspective exploded view of a midsole.

FIG. 26 is a perspective exploded view of a Midsole 68 of a shoe with a Midsole Stud Bolt Insert 88 on the medial, lateral and heel portions of the midsole. Each Stud Bolt 52 is shown protruding from the Midsole Stud Bolt Insert 88. Alternatively, other types of mountable and adjustable inserts can be used.

Figure 27:
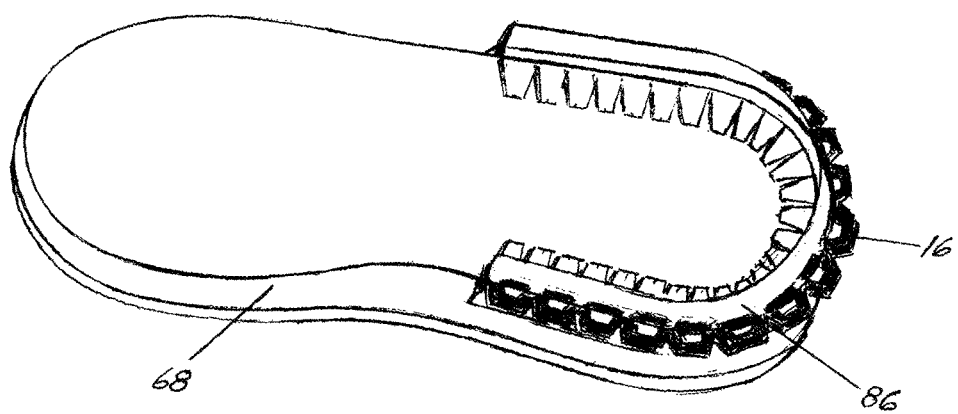
FIG. 27 is a perspective view of the midsole.

FIG. 27 is a perspective view of the Midsole 68 of a shoe with a Slots Track Strip 16 with multiple Slot 61 attachment means extending around the Midsole 68 from the medial side to the lateral side and layered on top of the midsole, attachable between the midsole and the shoe upper.

FIG. 28 is a perspective view of the Midsole 68 of a shoe with a Base Track Midsole Insert 94 with sections of the insert protruding from the midsole exposing a section of a Slide-on Track 58 the medial side, lateral side, and posterior heel portion of the shoe. The Base Track Midsole Insert 94 construction consists of the three side segments of the Slide-on Track 58 connectively reinforced and intersected beneath the heel portion of the Midsole 68.

FIG. 29 shows an overhead view of the Base Track Midsole Insert 94 showing the reinforcement portions connecting the medial side and lateral side approximately at the mid-foot section of the midsole, and connecting the medial side, lateral side, and posterior heel portions directly beneath the heel portion of the Midsole 68. The illustration also shows the medial, lateral, and posterior heel sections of the Slide-on Track 58.

FIG. 30 shows a heel side view of the Base Track Midsole Insert 94 showing the medial, lateral, and posterior heel sections of the Slide-on Track 58.

FIG. 31 shows a medial side view of the Base Track Midsole Insert 94 showing the Slide-on Track 58 medial side portion of the insert and posterior heel part of the insert. The illustration also shows the medial, and posterior heel sections of the Slide-on Track 58.

FIG. 32 shows a posterior angle view of a basketball shoe illustrating a Rack System 62 consisting of several parts including medial side flexed Support Bar 10, posterior heel flexed Support Bar 10 and lateral side flexed Support Bar 10 positioned on the Slots Track Strip 16 which slides onto and mounts on the Collar Track 14 and the Base Track 12, extending around the shoe collar and around the posterior shoe portion of the midsole. A series of Click Indents 48 along the lengths of the Collar Track 14 and Base Track 12 engage the matching Click Nubs 49 on the inside of the Slots Track Strip 16 as it slides into place. In this illustration, the Base Track 12 is embedded in the Midsole 12. Each Support Bar 10 shows a Collar Mounting End 18 and a Base Mounting End as well as Ribs 24 on a Flex Point 22.

FIG. 33 is a medial side view of a basketball shoe showing flexed removable multi-directional Bladder Type Support Bar 28 adjustably mounted at the Collar Mounting End 18 by selected Slot Track Strip 16 placement along a Collar Track 14 and aligned semi-perpendicular to the Collar Track 14 on the shoe upper with the distal Base Mounting End 20 of the Bladder Type Support Bar 28 mounted to a Base Track 12 which is embedded in the midsole of the shoe. Alternatively a combination or Blade Type Support Bar 30 could be used. The illustration shows the closure side of a padded or inflatable Extended Tongue Support Collar 66 wrapping the proximity of the leg above the ankle using a closed hook and loop closure system on the medial side of the shoe. On the Achilles heel portion of the shoe, the lengthened Bladder Type Support Bar 28 extends beyond the Collar Track 14 and is inserted through or attached to a Guide Ring 78 on the posterior heel portion of the Collar Track 14 and attaches to the posterior portion of the closed Extended Tongue Support Collar 66 with Snap Fastener Socket 84 and Snap Fastener Stud 85 shown in FIG. 35. Alternative attachment means or could be hook and loop, or other insertion or adjustable securing means. The drawing also illustrates the various Bladder Type Support Bar 28 attachments including the Ribs 24 at the Flex Point 22 and the Collar Mounting End 18 and the Base Mounting End 20 mounted by utilizing the selected Slot Track Strip 16 placement along the Collar Track 14 and the Base Track 12. Also shown the Collar Closure Strap 26 is in a "closed" position passing though Cinch Ring 80 used to adjustably tighten and secure the collar strap to the Collar Track 14.

FIG. 34 is a lateral side view of a basketball shoe showing flexed removable multi-directional Bladder Type Support Bar 28 adjustably mounted at the Collar Mounting End 18 by selected Slot Track Strip 16 placement along the Collar Track 14 and aligned semi-perpendicular to the Collar Track 14 on the shoe upper with the distal Base Mounting End 20 of the Bladder Type Support Bar 28 mounted to a Base Track 12 which is embedded in the midsole of the shoe. The illustration shows a padded or inflatable Extended Tongue Support Collar 66 wrapping the proximity of the leg above the ankle using a closed hook and loop closure system on the medial side of the shoe. On the Achilles posterior heel portion of the shoe, the lengthened Bladder Type Support Bar 28 extends beyond the Collar Track 14 and is inserted through or attached to a Guide Ring 78 adjacent to the Collar Track 14 and attaches to the closed Extended Tongue Support Collar 66 with Snap Fastener Socket 84 and Snap Fastener Stud 85 shown in FIG. 35. Alternative attachment means can be by hook and loop or other insertion, or other adjustable securing means. The drawing also illustrates the various Bladder Type Support Bar 28 attachments including the Ribs 24 at the Flex Point 22 and the Collar Mounting End 18 and the Base Mounting End 20 mounted by utilizing the selected Slot Track Strip 16 placement along the Collar Track 14 and the Base Track 12. Also shown is the Collar Closure Strap 26 in a "closed" position and the Cinch Ring 80 attached to the Collar Track 14. Alternatively a combination or Blade Type Support Bar 30 could be used.

FIG. 35 is a posterior heel side view of a basketball shoe with each flexed removable multi-directional Bladder Type Support Bar 28 adjustably mounted at the Collar Mounting End 18 by selected Slot Track Strip 16 placement along a Collar Track 14 and aligned semi-perpendicular to the Collar Track 14 on the shoe upper with the distal Base Mounting End 20 of the Bladder Type Support Bar 28 mounted to a Base Track 12 which is embedded in the midsole of the shoe. As shown, a lengthened Bladder Type Support Bar 28 is mounted on the posterior Achilles heel portion. The Bladder Type Support Bar 28 on the posterior Achilles heel portion extends to the height of the Extended Tongue Support Collar 66, illustrated here in an "open" position with securing ends extended in a "wing" type position. The Loops 76 portion is positioned on one end of the Extended Tongue Support Collar 66 and the Hooks 74 portion positioned on the opposite end. To "close", Snap Fastener Stud 85 attachments on the Extended Tongue Support Collar 66 snap into the Snap Fastener Socket 84 attachments on the extended Bladder Type Support Bar 28 or alternatively, with an extended Blade Type Support Bar 30. The lengthened Bladder Type Support Bar 28 on the posterior Achilles heel portion, illustrated "un-attached" to the Extended Tongue Support Collar 66, extends beyond the Collar Track 14 and is inserted through or attached to a Guide Ring 78 adjacent to the Collar Track 14 and attachable with Snap Fastener Stud 85 and Snap Fastener Socket 84 attachment means or could alternatively be attached by hook and loop or other insertion, attachment or securing means. The support bar on the posterior heel portion of the shoe "Achilles" is a combination elastic and flex support designed to absorb displaced force and reduce damaging range of motion and stress on the Achilles tendon and to assist with stability, when jumping, landing, and pivoting or leveraging off the foot. The Extended Tongue Support Collar 66 can have an expanded padding or air pocket for displacing and reducing force and stress on the Achilles tendon as the elastic property of the rear support bar is engaged and compensating for the tensile strength of the Achilles tendon when the wearer engages the foot in a pivoting motion from a standstill or while running or "cutting" or "planting" the foot.

FIG. 36 shows the medial side view of a basketball shoe with flexed removable multi-directional Support Bar 10 adjustably mounted to the medial side and on the rear Achilles heel portion. The illustration shows an Attachable Mesh Cover 92 attached by hook and loop closure or zipper, protecting the support bars and entire rear portion of the shoe. The removable cover can also be constructed of other material.

FIG. 37 shows the lateral side view of a basketball shoe with flexed removable multi-directional Support Bar 10 adjustably mounted to the medial side and to rear Achilles heel portion. The illustration shows an Attachable Mesh Cover 92 attached by Hooks 74 and Loops 76 closure or zipper, protecting the support bars and entire rear portion of the shoe. The removable cover can also be constructed of other material.

FIG. 38 is a rear heel view of a basketball shoe with flexed removable multi-directional Support Bar 10 adjustably mounted to the medial side, to the lateral side and to the rear Achilles heel portion. The illustration shows an Attachable Mesh Cover 92 attached by hooks and loops closure or zipper, protecting the support bars and entire rear portion of the shoe. The removable cover can also be constructed of other material.

Other types of materials and construction utilized can be utilized in the construction of Support Bar 10. For example, a Blade Type Support Bar 30 is constructed and configured with a solid yet flexible material resistant to breaking, such as carbon fiber enabling a greater amount of energy to be stored when the Blade Type Support Bar 30 is flexed and imparting a greater amount of resistance support. Athletes in various sports activities such as basketball and football may weigh in excess of 250 pounds and because of that additional weight greater forces are exerted on their feet and footwear while engaging in their chosen sport. The Blade Type Support Bar can also be constructed with a Flex Point 22 to facilitate flexing or can be concave or convex or of other shapes or angles to facilitate directional torsion flexing.

A Bladder Type Support Bar 28 is constructed using a flexible material that forms a bladder that can be inflated or injected with pressurized air, gas, or gel filling. The bladder may be formed using hollow extruded tube shaped plastic with the limb compartments pressurized and sealed using a Weld 38. Or, the bladder can also be formed using molded inflatable injected parts. The injection pressure can be measured in PSI (pounds per square inch). The use of high-pressure air or gas in the Bladder Type Support Bar 28 enables a lightweight yet durable construction. The use of high-pressure gel filling provides additional shock absorption properties to the Bladder Type Support Bar 28. The Bladder Type Support Bar 28 has a Flex Point 22 to facilitate the flexing and has a section of Ribs 24, bendable and expandable and enabling both expansion support resistance and directional torsion control.

The expansion of the Ribs 24 on the Bladder Type Support Bar 28 also function as a spring when stretched from its resting state or equilibrium.

Hooke's law for a spring states that F is the restoring reaction force exerted by the spring on whatever is pulling its free end. In that case the equation becomes $$F=-kX$$

The direction of the restoring force on the Ribs 24 on the Bladder Type Support Bar is opposite to that of the displacement and its elastic potential energy will also be influenced by the effect of producing vacuum when the Ribs 24 expand on a sealed high-pressure tube or compartment.

The Bladder Type Support Bar 28 can be pre-filled with injected air, gas, gel or other Bladder Filler Material 40 or injected with air or gas to a PSI selected according to the user's activity needs and maintained by the user when mounted on footwear. The Bladder Type Support Bar can also be filled with Bladder Filler Material 40 such as miniature balls, beads, pellets or other shaped filler materials such as cell-closed polystyrene foam encapsulated in a one-piece mold or sealed tube with Weld 38 sealing the bladder on the Collar Mounting End 18 and a Weld 38, sealing the bladder on the Collar Mounting End. Filler Material 40 can be lightweight and provide additional shock absorption properties when the Bladder Type Support Bar 28 is flexed and in use.

Each Support Bar 10, whether it is a Bladder Type Support Bar 28 or a Blade Type Support Bar 30 is attached to a Base Track 12 and a Collar Track 14. Each Support Bar 10 has a Collar Mounting End 18 and a Base Mounting End 20. The Support Bar 10 is positioned semi-perpendicular to these tracks by flexing the Support Bar 10 into position, creating the stored energy tension of a spring as the Collar Mounting End 18 and the Base Mounting End 20 are mounted respectively to the Collar Track 14 and the Base Track 12 in a tensioned "bow-like" manner. Alternatively, a deflated Bladder Type Support Bar 28 can be positioned by mounting the Collar Mounting End 18 to the Collar Track 14 and the Base Mounting End 20 to the Base Track 12 and then inflated with high-pressure air or gas. The Flex Point 22 and the Ribs 24 are inflated and the Bladder Type Support Bar 28 stores the energy tension of a spring, and depending upon the length of the Bladder Type Support Bar 28, the flex angle measurable from the Flex Point 22 to the top limb end of the Bladder Type Support Bar 28 is in a range of more than 90 degrees when flexed and equal to or less than 180 degrees when fully extended and un-flexed, and the flex angle measureable from the Flex Point 22 to the bottom limb end of the Bladder Type Support Bar 28 is in a range of less than 90 degrees to equal to or less than 0 degrees when fully extended and un-flexed, and with optimal support when inflated and flexed at a range of 150 degrees to 165 degrees for the top limb portion of the Bladder Type Support Bar 28 and 15 degrees to 30 degrees for the bottom limb portion of the Bladder Type Support Bar 28.

The Base Track 12, is inserted in the midsole, or between the midsole and shoe upper, and extends from the medial side of the shoe midsole around the heel portion to the lateral side of the shoe midsole forming a "horse shoe" shaped configuration.

The Collar Track 14 is attached to the collar portion of the midsole by stitching or other attachment means and extends from the medial side of the shoe collar around the heel portion of the shoe collar to the lateral side of the shoe collar, similarly forming "horse shoe" shaped configuration above and parallel to the Base Track 12.

This "horse shoe" type configuration of these two tracks provide multiple positions and spacing for adjustably securing a plurality of Support Bar 10 parts around the shoe from the mid-foot of the medial side and extending around the posterior of the heel and to the mid-foot are of the lateral side. This adjustable positioning enables Support Bar 10 placement at key locations along the upper and lower tracks pinpointing where the reciprocating and restoring reaction forces of multiple support bars, used in concert, are needed to help to maintain the foot in a safer, more neutral alignment as a wearer's leg is in motion and pivoting the ankle during a particular sports activity. Because the Support Bar 10 only contacts the shoe at the points in which it is specifically attached to the padded Collar Track 14 and the Base Track 12 and has a Flex Point 22 and Ribs 24 portion extending away from the shoe upper and the foot so as to not initiate unintended contact or pressure against other regions of the shoe upper, foot or frictionally rub against the foot. In addition to providing support and helping to maintain the foot in a more neutral plane during walking and running, the support bars work in tandem to provide additional support when the feet engage in more sudden and aggressive movements, such as planting, pivoting, turning, jumping, and landing when forces and impact are significantly greater and the stability of the foot requires simultaneous multi-directional support.

During sports activities such as basketball, each foot is continuously and simultaneously engaging in different positions and movement. While running, stopping, starting, pivoting, jumping, and landing, weight is constantly shifting between the right and left foot. In such position engagements, maintaining support and foot stability, as well as alignment, is critical to improving performance and to reduce the incidence of injury.

For example, the right foot of a running athlete may be suddenly "planted" creating an excessive eversion force from weight bearing that causes the right foot to tend to "roll" in the direction of the shoe's lateral side. The Support Bar 10 positioned on the lateral side Collar Track 14 and Base Track 12 of the right foot returns additional direct support from the stored energy of the "spring" flexed support bar, counter-resisting the rolling motion along the high ankle portion of the foot where the Collar Mounting End 18 of the Support Bar 10 is attached on the Collar Track 14. Simultaneously, the Support Bar 10 positioned on the medial side Collar Track 14 and Base Track 12 of the of the right foot is stretched in the direction of the eversion and the resulting elastic return force is exerted in the direction opposite to the eversion by the stretched, expanded Ribs 24 section of the Flex Point 22, helping to resist the eversion rolling motion. The result is to help correct the alignment and return the right foot to a range in the neutral plane.

In this example, at the same time, the left foot is simultaneously pivoting to change direction, creating an excessive inversion force on the medial side of the left foot. The Support Bar 10 positioned on the medial side Collar Track 14 and Base Track 12 of the left foot returns additional direct support from the stored energy of the "spring" flexed support bar, counter-resisting the excessive inversion motion along the high ankle portion of the foot where the Collar Mounting End 18 of the Support Bar 10 is attached on the Collar Track 14. Simultaneously, the Support Bar 10 positioned on the lateral side Collar Track 14 and Base Track 12 of the of the left foot is stretched in the direction of the inversion and the resulting elastic return force is exerted in the direction opposite to the inversion by the stretched, expanded Ribs 24 section of the Flex Point 22 helping to resist the inversion rolling motion. The result is to help correct the alignment and return the left foot to a range in the neutral plane.

Then, the planted right foot may need to suddenly explosively pivot into a jumping motion after the left foot has already left the ground leaving all weight distributed solely on the right pivot foot. Although the Achilles tendon can sustain the force of approximately 1000 pounds, a sudden pivoting directional movement on one foot can exceed that threshold leading to stress related injury such as chronic conditions of Achilles tendonitis and even Achilles tearing. The Support Bar 10 positioned on the posterior of the heel box provides additional stability and support to the Achilles tendon by working in tandem with the support bars positioned on the medial side and lateral side. In this example, an exploding pivoting move on the right foot will momentarily bear all forces and the entire weight load. The Support Bar 10 positioned on the Achilles portion of the heel box functions like a "second" Achilles tendon by providing compensating and additional elastic tensile strength and diverting weight bearing forces into the flexed Support Bar 10. The Support Bar 10 placed on the posterior of the heel box has an Achilles Y Notch at the top and attaches to a segmented Collar Track 14 so as to not press directly against the Achilles tendon. As the wearer, pivots and jumps off the right foot, in this example, the Support Bar 10 on the posterior of the heel box, flexes the Ribs 24 section of the Flex Point 22 a result of the closed Collar Closure Strap 26 on the Collar Track 14 wrapping above or on the high ankle region. As the wearer pivots off the forefoot, the flexing of the Support Bar 10 supplements the tensile strength of the Achilles tendon, reducing stress and strain. Multiple Rib 24 sections, in series, can improve the elastic properties and shock absorption properties of the Support Bar 10 and. Finally, in the example, as the wearer lands on one or both feet, the multiple support bars function to help to stabilize and settle the feet into a safer neutral plane by controlling and resisting excessive forces of inversion and eversion.

By using multiple support bars to provide multi-directional support to the foot, the structure of the shoe is also better protected from excessive pronation and supination and forces that can compromise the shoe's structure leading to breakdown of shoe components such as the upper and midsole, and uneven wear on the outsole, leading to gait problems for walkers and runners.

A Rack System 32 can also be utilized in which the support bars are pre-mounted on the on a Slots Track 16 that slides onto the Collar Track 14 and on a Slots Track 16 that slides onto the Base Track 12. The Slots Track 16 has an underside with Click Nubs 49 that match Click Indents 48 on the slide-on Slots Track 16 to enable the one-piece, pre-mounted Rack System 32 to slide securely into place.

The positioning of multiple support bars along the Collar Track 14 and The Base Track 12 on the medial side of the foot compliment the positioning of support bars positioned on the lateral side of the foot. The height of the Flex Point 22 and number of Ribs 24 sections on each Support Bar 10 can also directionally influence movement when the support bars are used in parallel as a Flex Point 22 positioned higher or lower than the midpoint. The support bars dynamically distribute forces multi-directionally from the medial side to the lateral side and from the lateral side to the medial side as well as to and from the posterior side where a Support Bar 10 is positioned to support the Achilles.

A series of slots on a Slots Track 16 are incorporated end-to-end on the Base Track 12 and a series of slots on a Slots Track 16 are also incorporated end-to-end on the Collar Track 14 to provide for adjustable slotting, positioning and placement of the Support Bar 10 when it is attached to the Base Track 12 and Collar Track 14. Similarly, a Studs Bolt Track Strip 50 has a series of threaded bolts which can be utilized on the Collar Track 14 and the Base Track 12 for mounting the support bars by using Dual Ring Connector 46 ends to attach by using threaded wing-nuts, hex nuts, or driver-head nuts for easy and secure adjustment and secure positioning.

The Support Bar 10 can be also mounted on the Collar Track 14 and the Base Track 12 by utilizing stitching, clamps, hooks, wing nuts, ratchet buckle or other attaching means to facilitate adjustable and secure placement. The flexed Support Bar 10 can be attached to a Support Bar Frame 44 that is stitched or attached by other means to various portions of the upper on the medial side, lateral side and Achilles heel portion of the shoe with the Support Bar 10 that is pre-flexed and attached to the frame, functioning in the same manner as if it were mounted directly to the Collar Track 14 or Base Track 12.

On the medial side of the shoe, the Support Bar 10 is attached semi-perpendicular or oblique to the Base Track 12 by attaching the Base Mounting End 20 of the Support Bar 10 to the selected slots of the Slots Track 16 on the Base Track 12. The distal end of the flexed Support Bar 10 is attached semi-perpendicular or oblique to the Collar Track 14 by attaching the Collar Mounting End 18 of the Support Bar 10 to the selected slots on the Slots Track 16 on the Collar Track 14 forming a "bowed" or "flexed" Support Bar 10 which is mounted on the medial side of the shoe. The support bars and be of constructed of different materials and shapes and angles and are not limited to being attached in a semi-perpendicular manner, but can also be attached in any fore facing angle or rear facing angle on the medial of the shoe, depending upon the footwear application, the wearer's weight, and sports activity.

On the lateral side of the shoe, the Support Bar 10 is attached semi-perpendicular or oblique to the Base Track 12 by attaching the Base Mounting End 20 of the Support Bar 10 to the selected slots of the 16 Slots Track on the Base Track 12. The distal end of the flexed Support Bar 10 is attached semi-perpendicular or oblique to the Collar Track 14 by attaching the Collar Mounting End 18 of the Support Bar 10 to the selected slots on the Slots Track 16 on the Collar Track 14 forming a "bowed" or "flexed" Support Bar 10 which is mounted on the lateral side of the shoe. The support bars and be of constructed of different materials and shapes and angles and are not limited to being attached in a semi-perpendicular manner, but can also be attached in any fore facing angle or rear facing angle on the lateral of the shoe, depending upon the footwear application, the wearer's weight, and sports activity.

On the posterior heel portion of the shoe, a Support Bar 10 is attached semi-perpendicular to the Base Track 12 by attaching the Base Mounting End 20 of the Support Bar 10 to the selected slots of the 16 Slots Track on the Base Track 12. The distal end of the flexed Support Bar 10 is attached semi-perpendicular to the Collar Track 14 by attaching the Collar Mounting End 18 of the Support Bar 10 to the selected slots on the Slots Track 16 on the Collar Track 14 forming a "bowed" or "flexed" Support Bar 10 which is mounted on the Achilles heel portion of the shoe. Dual support bars can also be attached on the posterior heel portion on either side of the Achilles rather than one support bar that is centered on the posterior of the heel box. The rear heel box support bar can include a spaced opening or notch at the top collar mounting end of the support bar to reduce direct pressure on the Achilles tendon and have multiple elastic flex points with tensile strength properties equivalent to the Achilles tendon.

A lengthened Bladder Type Support Bar 28 can be mounted on the posterior Achilles heel portion that extends and attaches on the posterior to the height of an Extended Tongue Support Collar 66 that wraps the leg area of the lower calf. This version of a lengthened support bar enables additional Achilles tendon support by permitting greater front to back and back to front control and support on the leg area of the lower calf and supports the front to back movement of the leg while reducing direct stress on the Achilles tendon. During dorsiflexion of the foot, in which the knee is extended over the foot, there is less than a 90 degree angle between the front part of the foot and the shin, the elongated Bladder Type Support Bar 28 engages in resistance support by stretching the elastic lower portion of the support bar, expanding the Ribs 24 of the Flex Point 22. During plantarflexion of the foot, similar to the foot pressing on a gas pedal, there is a greater than 90 degree angle between the front part of the foot and the shin, the Bladder Type Support Bar 20 engages in resistance support by compressing the elastic lower portion of the support bar, and compressing the Ribs 24 of the Flex Point 22. The support bar on the posterior heel portion of the shoe "Achilles" is a combination elastic and flex support designed to absorb displaced force and reduce damaging range of motion and stress on the Achilles tendon and to assist with stability, when jumping, landing, and pivoting or leveraging off the foot. The collar track can have an expanded padding or air pocket for displacing and reducing force and stress on the Achilles tendon by engaging the elastic property of the rear support bar and compensating for the tensile strength of the Achilles tendon when the wearer engages the foot in a pivoting motion from a standstill or while running or "cutting".

Many different types of support bar and collar and base attachment means can be used in combination and are not limited to the following:

The Collar Mounting End 18 of the Support Bar 10 can be attached to the Base Track 12 by using a Dual Ring Connector 46 with each ring connector mounting over a threaded Stud Bolt 52 and then flexing the Support Bar 10 to attach the Dual Ring Connector 46 of the Collar Mounting End 18 by mounting each ring connector over a threaded Stud Bolt 52. The Support Bar 10 is then secured by a Driver Head Nut 54 or a Hex Nut 56 or any threaded wing type nut, turned down on each threaded Stud Bolt 52 protruding through the Dual Ring Connector 46 openings. A Stud Bolts Track Strip 50 slides onto the Slide-on Track 58. The Stud Bolts Track Strip 50 has multiple Stud Bolt 52 selectable options for adjusting the placement of the Dual Ring Connectors to facilitate placement of the Support Bar 10.

The Collar Mounting End 18 of the Support Bar 10 attaches to the Base Track 12 by using a single or multiple Slot Hook 60 that hook a single or multiple Slot 61 protruding along a Slot Hook Track Strip 86 that slides onto the Slide-on Track 58. The Slot Hook Track Strip 86 has multiple Slot 61 selectable options for adjusting the placement of the Slot Hook 60 to facilitate the placement of the Support Bar 10.

The Base Track 12 can also effectively be integrated to various configurations in the midsole or in the layer between the shoe upper and the midsole to provide a solid and secure means for mounting the Support Bar 10.

It is to be understood that the expression used in the preferred embodiments does not limit the spirit or scope of the invention.

I have alternate methods of embodying this invention as described below:

The multi-directional support system, and parts, including support bars, collar and base can be encapsulated in the shoe upper.

A one-piece support bar can extend around the entire heel counter portion of the shoe from medial to posterior to lateral side.

The collar and base tracks can be of various shapes and sizes and can be intermittently attached around the perimeter of the collar and base.

A support bar can be semi-rigid or semi-flexible.

A support bar can be of a concave or convex bow shape without a specific flex-point.

A support bar can be molded, cast, extruded, cut from, or constructed by 3-D printer using plastics or other durable, rigid, or flexible materials.

The flex and spring of the support bar can provide varying support pressure by the increasing or decreasing the degree of flex, changing the composition of the flex bar, and by changing the alignment angles of the flex bar.

The support bars can exert directional support pressure around the shoe enclosure by the varying angular degree of flex, composition of the flex bar, height of flex points, and construction design of the flex bars.

The support bars can encapsulate or be injected or inflated with miniature balls, beads, pellets or other shaped filler materials such as cell-closed polystyrene foam.

The support bars bladders can be molded or made by extruded or welded tubes.

The support bars can be of various shapes, sizes and angles.

The support bars can flex and support in multiple directions.

The support bars can utilize different colors to identify and match location placement on the shoe.

The support bar colors can also indicate different flex pressure support intensity.

The support bars can be of varying length on the medial, lateral, or heel sides of the foot to correspond to the varying heights of the shoe upper in which case the base and collar can be in segments of varying heights around the shoe.

The support bars can be partially or wholly attached to or stitched directly to the shoe upper.

The support bars can be attached to the collar track and base track by clamps or ratchet buckles or similar means at each end of the support bar which when closed, secure the support bar in place at the designated position.

Different types of support bars can simultaneously be used in different positions, including solid, hollow, notched, drilled, blade or bladder type, and filled with gel, gases or other filler materials inflating the support bars attached to the tracks.

A support bar can be constructed in combination or assembled in parts with various portions of the support bar constructed with solid, hollow, notched, drilled, blade type or bladder type.

Each support bar can individually be partially constructed of solid material, partially constructed of compressed gel filling of varying viscosity, or partially constructed of compressed gases, air or other filler materials.

The flex section of the support bars can be formed by a spring, coil, ribs, angular lever, zig-zag design, or twist or similar flexing means.

A support bar can be a compression-like cylinder whereby one sealed limb portion, either top or bottom inserts into the other limb portion, resulting in plunged compressed air resistance.

The support bars can be made of flexible carbon fiber or other dense solid material, but it is not limited thereto.

The support bars can be made of polymers, plastics, or other flexible, elastic, lightweight materials, but it is not limited thereto.

The support bars can be made of porous or semi-porous material.

The support bar flex point can extend from any portion of the support bar or from any point or position from top to bottom of the support bar.

The support bars can be attached by various clamps, binder fasteners, hook-and-loop fasteners, snaps, buttons, ratchet buckles, or slot-slide closures but attachment means are not limited thereto.

The support bar can be straight, curved, angular or a combination thereof.

The support bar can be partially or wholly elastic.

A multiplicity of support bar types can be used simultaneously and be positioned interchangeably around the base/collar support tracks for varying types of support.

Base and collar tracks can be configured to accommodate a variety of support bar attachment means.

The base track can be removable and re-attachable.

The base track mounting can extend under the heel portion of the shoe and from medial side to lateral side.

The base track can form a heel cup under the heel portion of the shoe and extend from medial side to lateral side.

The base track can form a heel cup which interacts with the support bars by increasing the multi-directional pressure and support to the shoe as a result of heel strike or increased pressure to the heel portion of the shoe.

The base track can have extended support bar attachment points that protrude from the base.

The base track mounting can extend under the heel portion of the shoe and from medial side to lateral side.

The collar track can be removable and re-attachable.

The collar track can have extended support bar attachment points that protrude from the collar.

The collar track can be closed and attached by various binder latches, hook-and-loop fasteners, snaps, buttons, ratchet buckles, or rib and slot-slide closures, but attachment means are not limited thereto.

The collar track can be segmented or positioned at different heights on the shoe upper permitting higher or lower attachment points for support bars of different lengths on the medial, lateral, and posterior Achilles sides of the shoe.

Although the base and collar tracks facilitate mounting, securing, placement and ease of effectively positioning the support bars, functional attachment or mounting of the support bars can be made directly to the shoe by means of adhesive or glue, stitching, clamps, rivets, buttons, snaps, or any other attachment or mounting means to secure the support bar to the shoe.

The present invention is disclosed above and in the accompanying drawings with reference to a variety of embodiments. The purpose served by the disclosure, however, is to provide an example of the various features and concepts related to the invention, not to limit the scope of the invention. One skilled in the relevant art will recognize that numerous variations and modifications may be made to the embodiments described above without departing from the scope of the present invention, as defined by the appended claims.

That which is claimed is:

1. A support bar comprising;
   a resilient, flexible member of sufficient thickness and length with a plurality of limbs extending from a flex point at the middle portion, each limb so shaped and proportioned as to form attachable ends of the support bar;
   a means for attaching the support bar to an article of footwear, such that at least one limb of one end of the support bar attaches to a base portion of the article of footwear and at least one limb of the other end of the support bar attaches to a collar portion of the article of footwear;
   wherein when the attachable ends of the support bar limbs affix to the article of footwear, the support bar bends bowlike, tensioned in a state of flexion so as to store energy in the support bar.

2. The support bar as recited in claim 1, wherein the means for attaching the support bar to the article of footwear is selected from the group comprising stitching, adhesive, hook and loop, rivets, hooks, nut and bolt, slide and slot, ring connectors, clamps, fasteners, snaps, buttons, ties, binder latches, plug and receptacle, and ratchet buckles.

3. The support bar as recited in claim 1, further comprising;
   at least one fillable and sealable bladder compartment, so shaped and proportioned as to structurally reinforce the flexible and resilient support bar;
   at least one bladder compartment filler selected from the group comprising air, gas, liquid gel; and
   a resilient flex point portion when bended, stretched, twisted, and torqued.

4. The support bar as recited in claim 1, further comprising;
   at least one fillable and sealable bladder compartment, so shaped and proportioned as to structurally reinforce the flexible and resilient support bar;
   at least one bladder filler material of suitable shapes and sizes encapsulated in the bladder compartment, selected from the group comprising miniature beads, balls, pellets, grains, open cell foam and closed cell foam; and
   a resilient flex point portion when bended, stretched, twisted, and torqued.

5. The support bar as recited in claim 1, said support bar constructed and arranged such that the plurality of limbs adjustably and detachably attach to the means for attaching on the article of footwear, the positions of the means for attaching each support bar selected from the group comprising the medial side, the lateral side, and the posterior heel side.

6. The support bar as recited in claim 1, further comprising at least one geometric cut-out means on at least one limb portion to facilitate directional flex, reduce weight, and provide additional structural integrity.

7. The support bar as recited in claim 1, further comprising;
   the flex point with resilient means for flexing, stretching, and returning energy, selected from the group comprising ribs, springs, vacuum, and compression;
   wherein the support bar, attached and tensioned in a state of flexion on the article of footwear, influences the range of movement of the wearer's foot within the article of footwear, as the flex point of the support bar is engaged by the directional movement of the plurality of limbs attached to the structure of the article of footwear, directing resistance and counter-resistance support to and from positions where the attachable ends of the support bar attach to the means for attaching on the article of footwear.

8. The support bar as recited in claim 1, for providing multiple directions of support to the foot and ankle, further comprising;
   at least one resilient, flexible member of size and shape with attachable ends;
   a plurality of means for attaching to the article of footwear extending around the perimeter of the collar portion of a heel box from the medial side to the posterior side to the lateral side for positioning the support bar and adjustably and detachably receiving the attachable ends of the flexible member;
   a plurality of means for attaching to the article of footwear extending around the perimeter of the base portion of the heel box from the medial side to the posterior side to the lateral side for adjustably and detachably receiving the attachable ends of the flexible member; and
   adjustably and detachably attaching at least one of the attachable ends of the flexible member to at least one of the means for attaching on the base portion of the article of footwear and at least one of the attachable ends of the flexible member to at least one of the means for attaching on the collar portion of the article of footwear such that the flexible member bridges from the base portion of the article of footwear to the collar portion of the article of footwear in a bowlike state of flexion so as to store energy in the support bar.

9. The support bar as recited in claim 8, further comprising;
   a color scheme to identify the resiliency level rating of each support bar; and
   a color scheme to identify the positional placement of each support bar on the article of footwear; and
   each means for attaching on the article of footwear with a color scheme to identify and match the positional placement color scheme of each support bar.

10. The support bar as recited in claim 8, further comprising;
    the resilient, flexible member having at least one flex point portion constructed and arranged with means to facilitate flexing of the flex point portion, the means selected from the group comprising ribs, indentation, groove and recesses;

at least one of the plurality of limbs forming each end of the resilient, flexible member, each limb with attachable ends to attach to the means for attaching on the article of footwear;

at least one of the plurality of limbs extending from the flex point portion attached angular to the front collar portion of the article of footwear;

at least one of the plurality of limbs extending from the flex point portion attached angular to the rear base portion of the article of footwear;

such that at least one of the plurality of limbs of the proximal end of the resilient, flexible member attaches to the front collar portion of the article of footwear and at least one of the plurality of limbs of the distal end of the resilient, flexible member attaches to the rear base portion of the article of footwear; and the means for attaching each end of each limb of the resilient, flexible member to the article of footwear such that the limbs are attached in angular alignment and the resilient, flexible member is secured bowlike in a state of flexion so as to store energy in the resilient, flexible member and return resistance when the resilient, flexible member is bended.

11. The support bar as recited in claim 10, further comprising at least two resilient, flexible members positioned on and attached to the article of footwear in tandem to provide additional stability and support, each position of each individual resilient, flexible member selected from the group comprising the lateral side of the article of footwear, the medial side of the article of footwear, and the posterior heel side of the article of footwear.

12. The support bar as recited in claim 8 for providing support to the foot and high ankle, further comprising;

the support bar having a lengthened top portion and a bottom portion;

the top portion of the support bar having at least one limb lengthened and extending above the collar portion of the article of footwear to the high ankle;

the bottom portion having at least one of the plurality of limbs of the support bar attached to means for attaching on the base portion of the heel box of the article of footwear and said bottom portion of the support bar having the flex point;

a lengthened tongue of the article of footwear so shaped and proportioned as to extend to the high ankle;

at least two wing ends extending from the unattached end of the tongue, the wing ends overlapping and wrapping the high ankle;

attachment means on at least one of the wing ends, the attachment means selected from the group comprising snap fastener, hook and loop, and buttons;

a closure means for adjustably and detachably securing the overlapping wing ends, the closure means selected from the group comprising hook and loop, snap fastener, stud and socket, buttons and buckle fasteners;

the attachment means on at least one of the wing ends wrapping the back of the high ankle, configured and arranged so as to adjustably and detachably attach at least one limb of the top portion of the support bar;

the means for attaching on the posterior heel base portion of the article of footwear configured and arranged so as to adjustably and detachably attach at least one limb of the bottom portion of the support bar; and a loop guide attached to the posterior collar portion of the article of footwear such that the top portion of the support bar vertically and freely slides through the loop guide to the attachment means on the wing ends of the tongue wrapping the high ankle, the loop guide serving to elastically engage and flex the bottom portion of the support bar, wherein the flex point portion of the bottom portion of the support bar is directed away from the posterior heel portion of the article of footwear in a bowlike state of flexion so as to store energy in the support bar.

13. The support bar as recited in claim 8 for providing support to the article of footwear, further comprising;

a collar track extending around the heel box of the article of footwear from the medial side to the posterior side to the lateral side;

a base track, embedded in the midsole and extending around the heel box of the article of footwear from the medial side to the posterior side to the lateral side;

the collar track further comprising a series of means for attaching and adjustably positioning at least one limb of the support bar, said means selected from the group comprising hook and loop, rivets, hooks, nut and bolt, slide and slot, clamps, fasteners, snaps, buttons, binder latches, plug and receptacle, and ratchet buckles;

the base track further comprising a series of means for attaching and adjustably positioning at least one limb of the support bar, said means selected from the group comprising hook and loop, rivets, hooks, nut and bolt, slide and slot, ring connectors, clamps, fasteners, snaps, buttons, binder latches, plug and receptacle, and ratchet buckles;

the collar attachable end of the support bar adjustably and detachably attached to the collar track;

the base attachable end of the support bar adjustably and detachably attached to the base track;

such that the support bar is configured and arranged so the attached collar attachable end and the attached base attachable end bridges the length of the support bar from collar track to base track, such that the attached support bar is tensioned and flexes bow-like from end to end in a state of flexion.

14. The support bar as recited in claim 13, further comprising;

a slots track strip with attachment means to attach to the collar track, extending around the heel box of the article of footwear from the medial side to the posterior side to the lateral side, said means selected from the group stitching, adhesive, snaps, slide and slot, hook and loop, plug and receptacle, binder latches, fasteners and tongue and groove;

a slots track strip with attachment means to attach to the base track, extending around the heel box of the article of footwear from the medial side to the posterior side to the lateral side, said means selected from the group stitching, adhesive, snaps, slide and slot, hook and loop, plug and receptacle, binder latches, fasteners and tongue and groove; and each slots track strip further comprising a series of means for attaching for adjustably positioning and detachably attaching at least one limb of the support bar, the means for attaching selected from the group comprising hook and loop, hooks, nut and bolt, slide and slot, clamps, ring connectors, fasteners, snaps, buttons, binder latches, plug and receptacle, and ratchet buckles.

15. The support bar as recited in claim 13, further comprising a closure device on the collar track, and the ends of the collar track are secured together by an attachment means selected from the group comprising hook and loop, fasteners, snaps, buttons, ties, binder latches, ratchet buckles, ring connectors, and rib and slot-slide closures.

16. The support bar as recited in claim 13, further comprising at least one base track midsole insert contained in the midsole of the heel portion of the article of footwear, configured and arranged as a connective reinforcement intersecting with a segment of slide-on track on the medial side, on the lateral side, and on the posterior side.

17. The support bar as recited in claim 13, further comprising;
at least one midsole insert with a means for attaching protruding on the on the medial side of the heel portion to attach at least one limb of a support bar, the means for attaching selected from the group comprising, threaded stud, receptacle, binder latch, slot-slide and ratchet buckle fasteners;
a midsole with at least one cavity on the medial side of the heel portion shaped and arranged so as to receive the midsole insert;
at least one midsole insert with a means for attaching protruding on the on the lateral side of the heel portion to attach at least one limb of the support bar, the means for attaching selected from the group comprising, threaded stud, receptacle, binder latch, slot-slide and ratchet buckle fasteners;
a midsole with at least one cavity on the lateral side of the heel portion shaped and arranged so as to receive the midsole insert;
at least one midsole insert with a means for attaching protruding on the on the posterior side of the heel portion to couple to at least one limb of the support bar, the means for attaching selected from the group comprising, threaded stud, receptacle, binder latch, slot-slide and ratchet buckle fasteners; and
a midsole with at least one cavity on the posterior side of the heel portion shaped and arranged so as to receive the midsole insert.

18. The support bar as recited in claim 13, further comprising;
a base track strip with a plurality of means for attaching, extending around the perimeter of the heel portion of the midsole from the medial side to the posterior side to the lateral side; and
a means for securing the base track strip to the base of the article of footwear, the means layered on top of the midsole, attachable between the midsole and the upper of the article of footwear.

19. The support bar as recited in claim 13, further comprising a base track midsole insert unit embedded inside the midsole directly below the heel portion of the article of footwear, constructed and arranged with a plurality of reinforcement segments intersecting the midsole insert such that at least one segment connects from the central portion of the midsole insert to the medial side, at least one segment connects from the central portion of the midsole insert to the posterior side and at least one segment connects from the central portion of the midsole insert to the lateral side, configured and arranged such that each segment protrudes from the midsole and each segment has means for attaching at the protruding end.

20. The support bar as recited in claim 13, further comprising;
a mountable rack frame configured and arranged as to securely attach to the heel box portion of the article of footwear, further comprising;
an upper rack frame with means for attaching to the collar portion of the article of footwear;
a lower rack frame with means for attaching to the base portion of the article of footwear;
a plurality of attachable slots track strips, each slots track strip further comprising a series of means for adjustably positioning and attaching at least one limb of the support bar;
a collar track on the upper rack frame portion with means to secure the slots track strip as a unit, the means selected from the group comprising stitching, adhesive, hook and loop, rivets, hooks, nut and bolt, slide and slot, tongue and groove, ring connectors, click nubs, clamps, fasteners, snaps, buttons, binder latches, plug and receptacle, and ratchet buckles;
a base track on the lower rack frame portion with means to secure the slots track strip as a unit, the means selected from the group comprising stitching, adhesive, hook and loop, rivets, hooks, nut and bolt, slide and slot, tongue and groove, ring connectors, click nubs, clamps, fasteners, snaps, buttons, binder latches, plug and receptacle, and ratchet buckles;
the slots track strip configured and proportioned so as to attach to the collar track on the upper portion of the rack frame;
the slots track strip configured and proportioned so as to attach to the base track on the lower portion of the rack frame;
at least one support bar with the plurality of limbs of size and shape so as to adjustably and detachably attach at least one limb of the collar attachable end of the support bar to any of the series of means for attaching on the slots track strip of the upper portion of mountable rack frame, and at least one limb of the base attachable end of the support bar to any of the series of means for attaching on the slots track strip of the lower portion of the mountable rack frame; and
at least one limb of the collar attachable end of the support bar attached to the slots track strip of the collar track and at least one limb of the base attachable end of the support bar to the slots track strip of the base track so as to bridge and tension the support bar in a bow-like state of flexion.

21. The support bar as recited in claim 8, further comprising an upper cover on both sides of and around the heel box portion of the article of footwear, encapsulating and protecting at least one support bar inside the upper cover, with means to attach and detach the upper cover, the means selected from the group comprising zipper, hook and loop, and snaps.

22. A method, using the support bar of claim 8, for exerting multiple directions of support to the article of footwear, the method comprising;
selecting a position along the perimeter of the heel box portion, comprising the medial side, the lateral side and the posterior side of the article of footwear such that the attachable ends of the support bar attach to means for attaching on the article of footwear so as to apply structural support at the selected position;
attaching one end of the support bar to the base portion of the article of footwear and the other end of the support bar to the collar portion so as to flex and tension the support bar to store energy in a bow-like state of flexion bridging the base portion to the collar portion of the article of footwear;
variably flexing, bending, stretching, torquing, compressing and decompressing the support bar in multiple directions as the movement of the structure of the article of footwear engages the resistance of the attached flexed support bar;

returning stored energy such that the flexing, bending, stretching, torquing, compressing and decompressing of the flexed support bar counter resists the directional forces and directional movement of the structure of the article of footwear; and supporting the structure of the article of footwear so as to reduce the range of motion of the wearer's foot within the article of footwear, control the directional movement thereof, and support the foot and ankle as the flexed support bar is engaged by the directional movement of the structure of the article of footwear, directing resistance and counter-resistance support to and from positions where the attachable ends of the support bar attach to the means for attaching on the article of footwear.

23. A method for making the support bar of claim 8, the method comprising;

constructing the resilient, flexible member of sufficient thickness and length;

shaping and proportioning the resilient, flexible member with the flex point portion and plurality of limbs;

configuring each limb of the resilient, flexible member with attachable ends;

arranging the plurality of limbs such that at least one of the limbs extends from the top of the flex point portion and at least one of the limbs extends from the bottom of the flex point portion to form the flexible support bar; and attaching the attachable ends of each limb to the means for attaching on the article of footwear, at least one limb attached to the base portion of the article of footwear and at least one limb attached to the collar portion of the article of footwear such that the support bar is structurally tensioned, bowlike in a state of flexion.

24. The method as recited in claim 23, further comprising;

forming the support bar with at least one fillable and sealable bladder compartment portion:

filling each bladder compartment of the support bar with at least one filler so as to facilitate resilient flexing, the filler selected from the group comprising air, gas, liquid gel, miniature beads, balls, pellets, grains, open cell foam and closed cell foam; and sealing each bladder compartment by inlet valve or weld to retain the filler.

25. The method of claim 23 for making the support bar further comprising;

the means for constructing the resilient, flexible member selected from the group comprising three-dimensional printing, injection molding, cutting lengths of formed extruded tube, compression molding, thermoforming, vacuum forming, laminating and die cutting; and using resilient, flexible, elastic, durable, and lightweight materials selected from the group comprising polymers, plastics, carbon fiber, or combinations thereof for construction of the resilient, flexible member.

* * * * *